(12) United States Patent
Banville et al.

(10) Patent No.: US 6,492,550 B2
(45) Date of Patent: Dec. 10, 2002

(54) ALPHA-SUBSTITUTED THIO, -OXO TRIFLUOROMETHYLKETONES AS PHOSPHOLIPASE INHIBITORS

(75) Inventors: Jacques Banville, St-Hubert (CA); Serge Plamondon, Ste-Catherine (CA); Yonghua Gai, Killingworth, CT (US); Neelakantan Balasubramanian, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 23 days.

(21) Appl. No.: 09/779,411

(22) Filed: Feb. 8, 2001

(65) Prior Publication Data

US 2002/0068722 A1 Jun. 6, 2002

Related U.S. Application Data

(60) Provisional application No. 60/186,095, filed on Mar. 1, 2000, and provisional application No. 60/183,620, filed on Feb. 18, 2000.

(51) Int. Cl.$^7$ ............................................. C07C 59/147
(52) U.S. Cl. .................. 562/577; 556/413; 562/426; 562/431; 562/471; 562/463; 560/11; 560/17; 560/53; 560/60; 560/140; 560/226; 560/190; 560/180; 560/174; 514/506; 514/557; 514/567
(58) Field of Search .................. 514/506, 557, 514/567; 560/39, 17, 61, 53, 60, 140, 226, 190, 180, 174; 568/306; 562/426, 431, 471, 463, 577

(56) References Cited

U.S. PATENT DOCUMENTS

| 5,453,443 A | 9/1995 | Perrier et al. ................. 514/570 |
| 5,866,318 A | 2/1999 | Rydel et al. .................... 435/4 |

FOREIGN PATENT DOCUMENTS

| JP | 09268153 A | 4/1996 |
| WO | WO 97/21676 | 6/1997 |
| WO | WO 98/08818 | 3/1998 |
| WO | WO 98/25893 | 6/1998 |
| WO | WO 99/15129 | 4/1999 |

OTHER PUBLICATIONS

Bruce D. Hammock et al, "Substituted Thiotrifluoropropanones as Potent Selective Inhibitors of Juvenile Hormone Esterase", Bestic. Biochem. Physiol., vol. 22 (1984), pp. 209–223.*

Koen PIM. Vanhessche et al, "Catalytic Asymmetric Synthesis of New Halogenated Chiral Synthons", Chem. Eur. J., vol. 3 (1997), pp. 517–522.*

I. P. Street, et al, "Slow– and Tight–Binding Inhibitors of the 85–kDa Human Phospholipase $A_2$," Biochemistry, 32, pp. 5935–5940, 1993.

K. M. Abdullah, et al, "Synthesis and Preparation of an Affinity Chromatography Column for the Purification of Cytosolic Phospholipase $A_2$," Bioorganic & Medicinal Chemistry Letters, 5(5), pp. 519–522, 1995.

D. L. Boger, et al, "Trifluoromethyl Ketone Inhibitors of Fatty Acid Amide Hydrolase: A Probe of Structural and Conformational Features Contributing to Inhibition," Bioorganic & Medicinal Chemistry Letters, 9, pp. 265–270, 1999.

P. Norman, "Medicinal Chemistry in Eastern England–Ninth Symposium," IDRUGS, 1(1), pp. 49–54, 1998.

* cited by examiner

Primary Examiner—Paul J. Killos
(74) Attorney, Agent, or Firm—David M. Morse

(57) ABSTRACT

Inhibitors of the cytosolic phospholypase A2 enzymes are provided which are of use in controlling a wide variety of inflammatory diseases. The inhibitors of the present invention have the general formula where X, Z, $X_1$, $R^1$, $R^2$, $R^a$ and $R^b$ are as defined in the specification.

9 Claims, No Drawings

ALPHA-SUBSTITUTED THIO, -OXO TRIFLUOROMETHYLKETONES AS PHOSPHOLIPASE INHIBITORS

CROSS-REFERENCE TO RELATED APPLICATIONS

This application claims the benefit of U.S. Provisional Application Ser. No. 60/186,095 filed Mar. 1, 2000 and No. 60/183,620 filed Feb. 18, 2000.

BACKGROUND OF THE INVENTION

I. Field of the Invention

The present invention relates to certain alpha-substituted thio and oxo trifluoromethylketone compounds, their salts, hydrates and derivatives thereof, a process for their preparation, intermediates useful in their preparation, pharmaceutical compositions containing them and such ketone compounds as inhibitors of phospholipase A2 enzymes that are involved in the human inflammatory diseases and are thus useful agents in the treatment of inflammatory diseases such as asthma, arthritis, inflammatory bowel disease and neurodegenerative diseases.

II. Background of the Invention and Description of the Prior Art

Inflammatory diseases of the skin, such as psoriasis and atopic dermatitis, afflict greater than 5% of the population. And the inflammatory disease such as asthma affects more than 10 million people in U.S. alone. Currently, the treatment of these disorders typically involves topical use or inhalation of corticosteroids and bronchodilators. However, these agents also have undesirable side effects such as skin atrophy which limit the duration of therapy. In addition, topical application of a drug is difficult for many patients where the affected area may be very large.

Phospholipase $A_2$ ($PLA_2$) is the common name for phosphatide 2-acylhydrolase which catalyzes the hydrolysis of the sn-2-acyl ester bond of phosphoglycerides and results in production of lysophospholipids and free fatty acids. When the fatty acid is arachidonic acid, further action by cyclooxygenase and 5-lipoxygenase enzymes results in eicosanoid production, which is implicated in inflammation, and leukotrienes which are linked to asthma. Lysophophospholipid metabolism results in production of platelet activating factor and both lysophospholipids and platelet activating factor also play a role in inflammation.

$PLA_2$ enzymes exist as secreted forms (MW~12,000–15,000) and cytosolic forms (MW~85,000). The cytosolic or $cPLA_2$ enzymes appear to play a key role in the pathway leading to the formation of platelet activating factor and the eicosanoids.

Inappropriate activation of the cytosolic $PLA_2$ enzymes, therefore, can result in a variety of chronic and acute conditions including asthma, cerebral ischemia [Clemens et al., *Stroke*, 1996, 27: 527–535], Alzheimer's Disease [Stephenson et al., *Neurobiology of Stroke*, 1996, 3: 51–63 and see also U.S. Pat. No. 5,478,857], rheumatoid arthritis, neutrophil and platelet activation [Huang et al., *Mediators of Inflammation*, 1994, 3: 307–308], chronic skin inflammation and damage to the skin resulting from exposure to ultraviolet light [Gresham et al., *American Journal of Physiology*, 1996, 270; *Cell Physiology*, 39: C1037–C1050] and macrophage activation [Balsinde et al., *Journal of Biological Chemistry*, 1996, 271: 6758–6765].

Inhibitors of the $cPLA_2$ enzymes may, therefore, be of use in controlling a wide variety of inflammatory diseases. The literature describes a significant number of compounds said to be phospholipase $A_2$ inhibitors.

*Biochemistry*, 1993, 32: 5935–5940, discloses a trifluoromethyl ketone analog of arachidonic acid having the formula

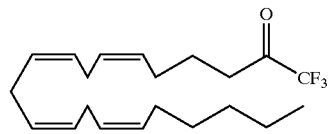

as a selective inhibitor of $cPLA_2$.

*Bioorganic Med. Chem. Lett.*, 1995, 5: 519–522, discloses selective cPLA2 inhibitors of the formula

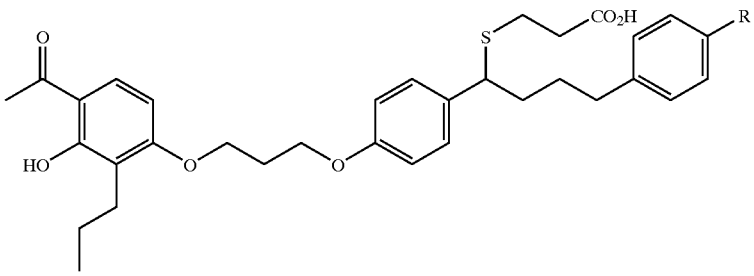

where R is either H or OH.

Japanese published Patent Application JP09268153A (Derwent No. 97-554679/51) discloses $cPLA_2$ inhibitors of the formula $RCOCF_3$ where RCO is an acyl residue of an n-3 series highly unsaturated fatty acid. The compounds are said to be useful as antiinflammatory or antiallergic drugs.

Certain trifluoromethylketone have been disclosed as inhibitors of fatty acidamide hydrolase in *Bioorg. & Med. Chem. Lett.*, 1999, 9: 265–270.

Published PCT Application WO 98/25893 discloses arylsulfonamide compounds of the general formula

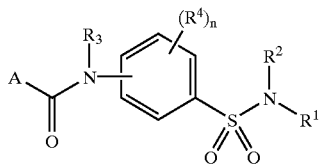

wherein:
A represents a $C_4$–$C_{10}$ alkyl group, an aryl group, an arylalkyl group, radicals selected from the group consisting of —CH=CH—B, —O—B, —S—B, and —NH—B, or radicals of formula —CH$_2$—X,
wherein:
B represents a non-aromatic $C_3$–$C_8$ carbocycle, a $C_3$–$C_8$ alkyl group, a heterocycle or an arylalkyl group, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and
X is a member selected from the group consisting of a halogen atom, —S-aryl, —S-heterocycle, and —PO$_3$R$_2$ wherein each R is independently selected from the group consisting of a hydrogen atom and $C_1$–$C_3$ alkyl;
$R^1$ and $R^2$ each independently represent a hydrogen atom, a lower alkyl group, or a group represented by the formula: —(CH$_2$)$_q$—A' wherein q is an integer of 2 to 4, and A' is a member selected from the group consisting of a hydroxyl group, a group represented by the formula:

wherein $R^5$ and $R^6$ each independently represent a hydrogen atom, a lower alkyl group, or a group represented by the formula:

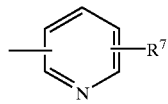

wherein $R^7$ represents a hydrogen atom, a lower alkyl group, or a group represented by the formula:

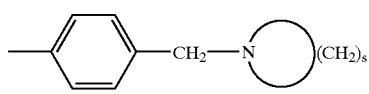

wherein s is an integer of 2 to 5; or
$R^1$ and $R^2$ each independently represent an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

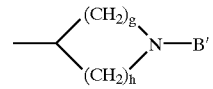

wherein g and h are each an integer of 1 to 4, and B' stands for a lower alkyl group, an arylalkyl group, an arylalkyl group substituted by lower alkyl; halogen or a lower alkoxy group, or a pyridylalkyl group, or a pyridylalkyl group substituted with a lower alkyl group, a halogen or a lower alkoxy group; or
$R^1$ and $R^2$ may be combined together to form a 6- or 7-membered ring which may contain a nitrogen or oxygen atom in addition to the nitrogen atom to which $R^1$ and $R^2$ are bonded, and said 6- or 7-membered ring may be substituted with a lower alkyl, arylalkyl, cycloalkylalkyl or heteroarylalkyl group;
$R^3$ represents a hydrogen atom, a lower alkyl group, or a $C_3$–$C_8$ cycloalkyl group;
$R^4$ represents a hydrogen atom, a lower alkyl group, a lower alkoxy group or a halogen atom;
n is an integer of 1 to 4, provided that when n is 2, the two $R^4$ groups may form a cyclohexenyl or phenyl ring together with two adjacent carbon atoms constituting the benzene ring; and any pharmacologically acceptable salts thereof as inhibitors of phospholipase A$_2$ activity, particularly cPLA$_2$.

The published PCT Application WO 98/08818 discloses Inhibitors of phospholipase enzymes of formulae I, II and III.

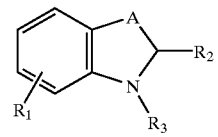

I

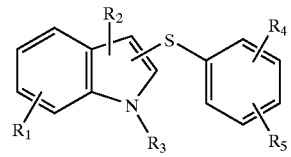

II

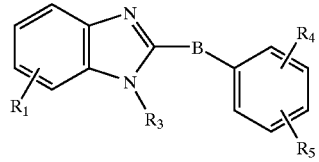

III or a pharmaceutically acceptable salt thereof, wherein:
A is independent of any other group and is selected from the group consisting of —CH$_2$— and —CH$_2$—CH$_2$—;
B is independent of any other group and is selected from the group consisting of —(CH$_2$)$_n$—, —(CH$_2$O)$_n$—, —(CH$_2$S)$_n$—, —(OCH$_2$)$_n$—, —(SCH$_2$)$_n$—, —(CH=CH)$_n$—, —(C≡C)$_n$—, —CON(R$_6$)—, —N(R$_6$)CO—, —O—, —S—and —N(R$_6$)—;
$R_1$ is independent of any other R group and is selected from the group consisting of —X—R$_6$, —H, —OH—, halogen, —CN, —NO$_2$, $C_1$–$C_5$ alkyl, alkenyl, alkinyl, aryl and substituted aryl;

$R_2$ is independent of any other R group and is selected from the group consisting of —H, —COOH, —COR$_5$, —CONR$_5$R$_6$, —(CH$_2$)$_n$—W—(CH$_2$)$_m$—Z—R$_5$, —(CH$_2$)$_n$—W—R$_5$, —Z—R$_5$, C$_1$–C$_{10}$ alkyl, alkenyl and substituted aryl;

$R_3$ is independent of any other R group and is selected from the group consisting of —H, —COOH, —COR$_5$, —CONR$_5$R$_6$, —(CH$_2$)$_n$—W—(CH$_2$)$_m$—Z—R$_5$, —(CH$_2$)$_n$—W—R$_5$, —Z—R$_5$, C$_1$–C$_{10}$ alkyl, alkenyl and substituted aryl;

$R_4$ is independent of any other R group and is selected from the group consisting of —H, —OH, OR$_6$, SR$_6$, —CN, —COR$_6$, —NHR$_6$, —COOH, —CONR$_6$R$_7$, —NO$_2$, —CONHSO$_2$R$_8$, C$_1$–C$_5$ alkyl, alkenyl and substituted aryl;

$R_5$ is independent of any other R group and is selected from the group consisting of —H, —OH, —O(CH$_2$)$_n$R$_6$, —SR$_6$, —CN, —COR$_6$, —NHR$_6$, —COOH, —NO$_2$, —COOH, —CONR$_6$R$_7$, —CONHSO$_2$R$_8$, C$_1$–C$_5$ alkyl, alkenyl, alkinyl, aryl, substituted aryl, —CF$_3$, —CF$_2$CF$_3$ and

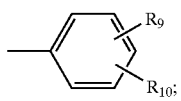

$R_6$ is independent of any other R group and is selected from the group consisting of —H, C$_1$–C$_5$ alkyl, alkenyl, alkinyl, aryl and substituted aryl;

$R_7$ is independent of any other R group and is selected from the group consisting of —H, C$_1$–C$_5$ alkyl, alkenyl, alkinyl, aryl and substituted aryl;

$R_8$ is independent of any other R group and is selected from the group consisting of C$_1$–C$_3$ alkyl, aryl and substituted aryl;

$R_9$ is independent of any other R group and is selected from the group consisting of —H, —OH, a halogen, —CN, —OR$_6$, —COOH, —CONR$_6$R$_7$, tetrazole, —CONHSO$_2$R$_8$, —COR$_6$, —(CH$_2$)$_n$CH(OH)R$_6$ and —(CH$_2$)$_n$CHR$_6$R$_5$;

$R_{10}$ is independent of any other R group and is selected from the group consisting of —H, —OH, a halogen, —CN, —OR$_6$, —COOH, —CONR$_6$R$_7$, tetrazole, —CONHSO$_2$R$_8$, —COR$_6$, —(CH$_2$)$_n$CH(OH)R$_6$ and —(CH$_2$)$_n$CHR$_6$R$_5$;

W is, independent each time used including within the same compound, selected from the group consisting of —O—, —S—, —CH$_2$—, —CH=CH—, —C≡C— and —N(R$_6$)—;

X is independent of any other group and is, independently each time used including within the same compound, selected from the group consisting of —O—, —S— and —N(R$_6$)—;

Z is independent of any other group and is, independently each time used including within the same compound, selected from the group consisting of —CH$_2$—, —O—, —S—, —N(R$_6$)—, —CO—, —CON(R$_6$)— and —N(R$_6$)CO—;

m is, independently each time used including within the same compound, an integer from 0 to 4; and n is independently of m and is, independently each time used including within the same compound, an integer from 0 to 4.

*Drugs*, 1998, 1(1): 49–50 discloses a limited series of cPLA$_2$ inhibitors as shown below

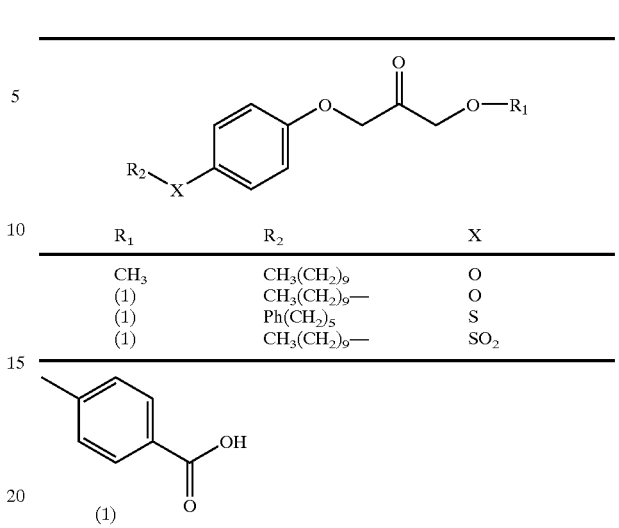

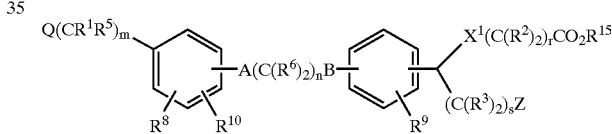

U.S. Pat. No. 5,866,318 relates to methods for inhibiting cell death in mammalian cells, particularly in neuronal cells, by administering a suitable inhibitor of phospholipase A$_2$ activity, typically an inhibitor of cPLA$_2$.

WO 97/21676 Patent discloses certain azetidinone compounds as phospholipase inhibitors in the treatment of atherosclerosis.

U.S. Pat. No. 5,453,443 discloses a series of biaryl ketones which are reported to inhibit PLA2 enzymes. These compounds have the generic formula wherein:

$R^1$ is selected from
(a) hydrogen,
(b) —C$_{1-6}$alkyl, and
(c) —C$_{1-6}$alkyl-phenyl;

or wherein $R^1$ and $R^5$ are joined such that together with the carbon atoms to which they are attached there is formed a saturated or unsaturated carbon ring of 3, 4, 5, 6, 7 or 8 atoms;

$R^2$ and $R^3$ are each independently selected from
(a) hydrogen,
(b) —C$_{1-6}$alkyl, and
(c) —C$_{1-6}$alkyl-phenyl;

or wherein two $R^2$ or two $R^3$ are joined such that together with the carbon atoms to which they are attached there is formed a saturated or unsaturated carbon ring of 3, 4, 5, 6, 7 or 8 atoms;

$R^5$ is as defined above or is selected from
(a) hydrogen,
(b) —C$_{1-6}$alkyl,
(c) —C$_{1-6}$alkyl-phenyl C$_{1-6}$alkyl,
(d) —OH,
(e) —O—C$_{1-6}$alkyl, or
(f) —O—C$_{1-6}$alkyl-phenyl C$_{1-6}$alkyl;

R⁶ is selected from
- (a) hydrogen,
- (b) —$C_{1-6}$alkyl,
- (c) —$C_{1-6}$alkyl-phenyl, wherein the phenyl is optionally substituted with $C_{1-2}$alkyl;
- (d) —OH,
- (e) —O—$C_{1-6}$alkyl, or
- (f) —$C_{1-6}$alkyl-phenyl, wherein the phenyl is optionally substituted with $C_{1-2}$alkyl;

or wherein two R⁶ are joined to form O= or are joined together such that together with the carbon atom to which they are attached there is formed a saturated or unsaturated carbon ring of 3, 4, 5, 6, 7 or 8 atoms;

$R^8$, $R^9$ and $R^{14}$ are each independently selected from
- (a) H,
- (b) —$C_{1-6}$alkyl,
- (c) halo,
- (d) —CN,
- (e) —OH,
- (f) —O$C_{1-6}$alkyl,
- (g) —O$C_{1-6}$alkyl-phenyl,
- (h) —$SR^{11}$,
- (i) $S(O)R^{11}$, or
- (j) $S(O)_2R^{11}$;

$R^{10}$, $R^{15}$, $R^{16}$ and $R^{17}$ are each independently selected from
- (a) hydrogen,
- (b) —$C_{1-6}$ alkyl, and
- (c) —$C_{1-6}$ alkyl-phenyl;

$R^{11}$ is selected from
- (a) —$C_{1-6}$ alkyl,
- (b) —$C_{2-6}$ alkenyl,
- (c) —$CF_3$,
- (d) -phenyl$(R^{12})_2$, or
- (e) —$C_{2-6}$ alkenyl-phenyl$(R^{12})_2$;

$R^{12}$ is
- (a) hydrogen,
- (b) —$C_{1-6}$ alkyl,
- (c) Cl, F, I or Br;

$R^{13}$ is perfluoro $C_{1-6}$alkyl;

A and B are each independently
- (a) covalent bond,
- (b) O,
- (c) S,
- (d) S(O), or
- (e) $S(O)_2$;

Q is selected from
- (a) —$CH(OH)R^{13}$,
- (b) —$COR^{13}$,
- (c) —$COR^{16}$, or
- (d) —$C_{1-4}$alkylCOCOO$R^{17}$;

$X^1$ is selected from
- (a) —O—,
- (b) —S—,
- (c) —S(O)—,
- (d) —$S(O)_2$—;

Z is
- (a) H, or
- (b) -phenyl-$(R^{14})_3$;

m is 0, 1, 2, 3 or 4;

n is 2, 3, 4, 5, 6 or 7; and r and s are each independently 0, 1, 2, 3, 4, 5, 6, 7 or 8.

Published application WO 99/15129 discloses selective cPLA₂ inhibitors having the formula

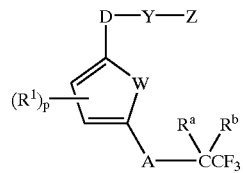

wherein W is CH=CH, CH=N, O or S;

$R^1$ is $(C_1-C_6)$alkyl, $(C_2-C_6)$alkenyl, $(C_2-C_6)$alkynyl, $(C_1-C_6)$alkoxy, $(C_1-C_6)$alkylthio, halo, hydroxy, cyano,

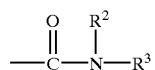

in which $R^2$ and $R^3$ are each independently hydrogen or $(C_1-C_6)$alkyl, —COO—$(C_1-C_6)$alkyl, $CF_3$, $(C_1-C_6)$ alkylphenyl, phenyl or phenyl substituted by one or more, preferably 1–3, of $(C_1-C_6)$alkyl, —COO—$(C_1-C_6)$alkyl,

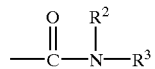

in which $R^2$ and $R^3$ are as defined above, halo, hydroxy, —O—$(C_1-C_6)$alkyl, —S—$(C_1-C_6)$alkyl or $(C_2-C_6)$ alkenyl;

p is 0, 1 or 2;

A is V—$(R^c)_n$—;

$R^c$ is a straight or branched chain alkyl group;

n is 0 or an integer of from 1 to 6;

$R^a$ and $R^b$ when taken together form an oxo (=O) group, or $R^a$ and $R^b$ are each independently hydrogen or OH;

V is O, —S—, —SO—, —$SO_2$, —CONH or NHCO when n is an integer of from 1 to 6 or V is $(C_2-C_6)$ alkenyl or a bond when n is 0 or an integer of from 1 to 6;

D is —$(CH_2)_m$ or a bond linking the

ring to Y;

m is an integer of from 1 to 6;

Y is —O—, —S—, —SO—, —$SO_2$;

or a bond;

$R^4$ is as defined below for $R^7$;
Z is

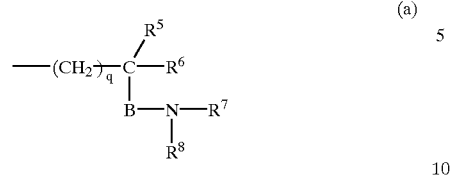 (a)

in which B is:

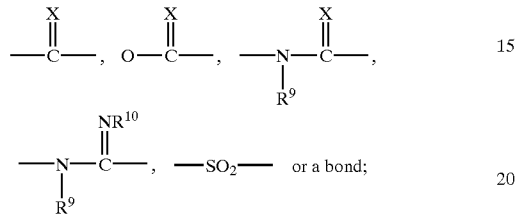

X is S or O;
q is an integer from 1 to 6;
$R^9$ is hydrogen or $(C_1-C_6)$alkyl;
$R^{10}$ is hydrogen, CN, $NO_2$, OH, —O—$(C_1-C_6)$alkyl, $(C_1-C_6)$ alkyl, phenyl or $(C_1-C_6)$alkylphenyl;
$R^5$ and $R^6$ are each independently hydrogen or $(C_1-C_{18})$ alkyl;
$R^7$ and $R^8$ are each independently
  (a) hydrogen;
  (b) $(C_1-C_{18})$alkyl;
  (c) $(C_1-C_{18})$alkyl substituted by one or more of
    (1) phenyl;
    (2) phenyl substituted by 1–5 fluoro, 1–3 (for each of the following phenyl substituents) halo (other than fluoro), 1–3 $(C_1-C_6)$alkoxy, 1–3$(C_1-C_6)$alkyl, nitro, cyano, hydroxy, trifluoromethyl, $(C_1-C_6)$ alkylthio, amino, 1–3 $(C_1-C_6)$ alkylamino, di$(C_1-C_6)$alkylamino, —$CO_2H$, —COO—$(C_1-C_6)$alkyl, —$SO_3H$, —$SO_2NHR^{15}$ in which $R^{15}$ is hydrogen or $(C_1-C_6)$alkyl, or

in which $R^2$ and $R^3$ are as defined above;
    (3) heterocyclic selected from oxadiazolyl, isoxazolyl, oxazolyl, furyl and thiazolyl;
    (4) heterocyclic substituted by one or more of, preferably 1–3, phenyl, phenyl substituted by 1–3 (for each of the following) halo, $(C_1-C_6)$alkoxy, $(C_1-C_6)$alkyl, nitro, cyano, hydroxy, trifluoromethyl, $(C_1-C_6)$alkylthio, amino, $(C_1-C_6)$alkylamino, di$(C_1-C_6)$alkylamino, $CO_2H$, —COO—$(C_1-C_6)$alkyl, —$SO_3H$, $SO_2NHR^{15}$ in which $R^{15}$ is hydrogen or $(C_1-C_6)$alkyl, or

in which $R^2$ and $R^3$ are as defined above, $(C_1-C_6)$ alkyl or $(C_1-C_6)$alkyl substituted by one or more, preferably 1–3, phenyl or heterocyclic groups, said phenyl or heterocyclic group being unsubstituted or substituted by 1–3 (for each of the following) halo, 1–3 $(C_1-C_6)$alkoxy, 1–3 $(C_1-C_6)$ alkyl, nitro, cyano, hydroxy, trifluoromethyl, $(C_1-C_6)$alkylthio, amino, 1–3 $(C_1-C_6)$alkylamino, di$(C_1-C_6)$alkylamino, COOH, —COO—$(C_1-C_6)$ alkyl, —$SO_3H$, —$SO_2NHR^{15}$ in which $R^{15}$ is hydrogen or $(C_1-C_6)$alkyl, or

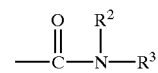

in which $R^2$ and $R^3$ are each independently hydrogen or $(C_1-C_6)$alkyl, the heterocyclic radical being selected from imidazolyl, oxadiazolyl, isoxazolyl, pyrrolyl, pyrazolyl, oxazolyl, furyl, thianyl or thiazolyl;

(5) carboxy or —COO—$(C_1-C_6)$alkyl;
(6) hydroxy, halo, —O—$(C_1-C_6)$ alkyl or —S—$(C_1-C_6)$alkyl, with the proviso that the OH, ethers or thioethers cannot be on the carbon bearing the heteroatoms;
(7) cyano;
(8) halo, trifluoromethyl or trifluoroacetyl;
(9) $CH_2$ L—$R^{16}$ in which L is

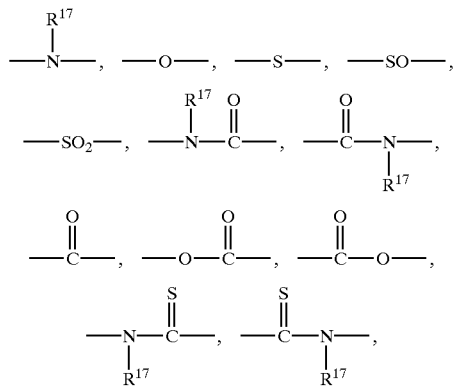

or —O—$SiR^{16}R^{18}R^{19}$ or a bond in which $R^{16}$ and $R^{17}$ are each independently $(C_1-C_{18})$alkyl or $(C_2-Cl_8)$alkenyl or $(C_1-C_{18})$alkyl or $(C_2-C_{18})$alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 $(C_1-C_6)$alkoxy, 1–3$(C_1-C_6)$ alkyl, nitro, cyano, hydroxy, 1–3 trifluoromethyl, 1–3 $(C_1-C_6)$alkylthio, amino, 1–3$(C_1-C_6)$alkylamino, 1–3 di$(C_1-C_6)$alkylamino, $CO_2H$, 1–3 —COO$(C_1-C_6)$ alkyl,

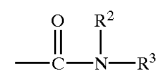

or —$SO_2NHR^9$ in which $R^9$ is hydrogen or $(C_1-C_6)$ alkyl and $R^2$ and $R^3$ are as defined above;

(b)

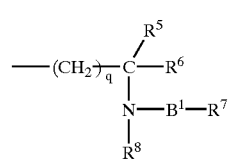

in which $B^1$ is

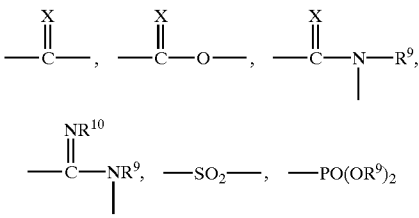

or a bond; providing that when $B^1$ is $-PO(OR^9)_2$, then $R^7$ becomes $R^9$, and when $B^1$ is

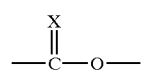

or $-SO_2-$, then $R^7$ cannot be hydrogen;

X, q, $R^5$, $R^6$, $R^7$, $R^8$, $R^9$ and $R^{10}$ are as defined in (a);

(c)

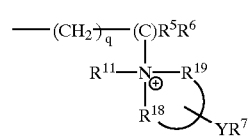

in which q, $R^5$ and $R^6$ are as defined above;

$R^{18}$, $R^{19}$ and $R^{11}$ are as defined above for $R^7$ and $R^8$ except that they may not be hydrogen, or $R^{18}$ and $R^{19}$ taken together with the nitrogen to which they are attached represent a 4, 5- or 6-membered heterocyclic ring and Y, $R^7$ and $R^{11}$ are as defined above, or $R^{18}$, $R^{19}$ and $R^{11}$ taken together with the nitrogen to which they are attached represent pyridinium, said pyridinium group being unsubstituted or substituted by $(C_1-C_{12})$ alkyl, $(C_1-C_{12})$alkoxy, amino, $(C_1-C_{12})$alkylamino, di$(C_1-C_{12})$alkylamino,

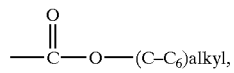

$-S-(C_1-C_{12})$alkyl,

in which $R^2$ and $R^3$ are as defined above, phenyl or phenyl $(C_1-C_{10})$alkyl;

(d)

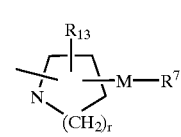

in which $R^{13}$ is $(C_1-C_{18})$alkyl or $(C_1-C_{18})$alkyl substituted by carboxy,

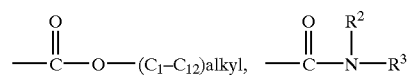

in which $R^2$ and $R^3$ are as defined above, hydroxy, $-O-(C_1-C_6)$ alkyl, $-O-(C_1-C_6)$ alkyl or $-S-(C_1-C_6)$ alkyl substituted by 1 or 2 phenyl or substituted phenyl groups, the substituents for the substituted phenyl groups being 1–5 fluoro or 1–3 (for each of the following phenyl substituents) halo (other than fluoro), $(C_1-C_6)$alkoxy, $(C_1-C_6)$alkyl, nitro, cyano, hydroxy, trifluoromethyl, $(C_1-C_6)$alkylthio, amino, $(C_1-C_6)$alkylamino, di$(C_1-C_6)$-alkylamino, $CO_2H$, COO—$(C_1-C_6)$ alkyl, $SO_3H$, $SO_2NHR^{15}$ in which $R^{15}$ is hydrogen or $(C_1-C_6)$ alkyl or

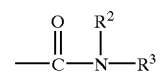

in which $R^2$ and $R^3$ are as defined above;

r is 0 or an integer of from 1 to 3;

$R^7$ is as defined above;

M is $-(CH_2-)_mT$ where

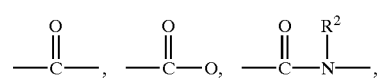

in which $R^2$ is as defined above, $-SO_2-$ or a bond when $MR^7$ is on nitrogen and providing that when

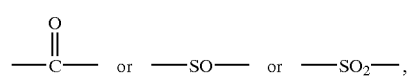

then $R^7$ cannot be hydrogen, and

T is $$-\overset{O}{\underset{\|}{C}}-, \quad -\overset{O}{\underset{\|}{C}}-O-, \quad -O-, \quad -S-,$$

$$-SO-, \quad -SO2-, \quad -\underset{|}{\overset{R^{14}}{N}}-$$

or a bond when $MR^7$ is on a carbon atom of the heterocyclic ring;

$R^{14}$ is hydrogen or $(C_1-C_6)$alkyl;

m is 0 or an integer of 1–6;

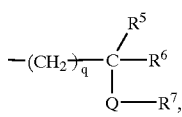
(e)

wherein Q is —O—, —S—, —SO— or —SO$_2$—, and q, $R^5$, $R^6$ and $R^7$ are as defined above, providing that when Q is —SO— or —SO$_2$—, $R^7$ cannot be hydrogen;

(f) $R^7$ wherein $R^7$ is defined above, providing that when Y is —SO— or —SO$_2$—, $R^7$ cannot be hydrogen; and $R^{18}$ and $R^{19}$ are phenyl or phenyl substituted by 1–3 halo, $(C_1-C_6)$alkoxy, $(C_1-C_6)$alkyl, nitro, cyano, hydroxy, trifluoromethyl, $(C_1-C_6)$alkylthio, amino, $(C_1-C_6)$alkylamino, di$(C_1-C_6)$alkylamino, CO$_2$H, —COO—$(C_1-C_6)$alkyl, —SO$_3$H, SO$_2$NHR$^{15}$ in which $R^{15}$ is hydrogen or $(C_1-C_6)$alkyl, or

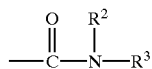

in which $R^2$ and $R^3$ are as defined above; or pharmaceutically acceptable salts, solvates or prodrugs thereof.

$R^{18}$ and $R^{19}$ are phenyl or phenyl substituted by 1–3 halo, $(C_1-C_6)$alkoxy, $(C_1-C_6)$ alkyl, nitro, cyano, hydroxy, trifluoromethyl, $(C_1-C_6)$ alkylthio, amino, $(C_1-C_6)$alkylamino, di$(C_1-C_6)$alkylamino, CO$_2$H, —COO—$(C_1-C_6)$alkyl, —SO$_3$H, SO$_2$NHR$^{15}$ in which $R^{15}$ is hydrogen or $(C_1-C_6)$alkyl, or

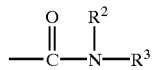

in which $R^2$ and $R^3$ are as defined above; or pharmaceutically acceptable salts, solvates or prodrugs thereof.

There is nothing in any of the foregoing references, or in the general prior art, to suggest the novel alpha substituted thio, oxo-trifluoromethyl-ketones of the present invention as cytosolic phospholipase A2 inhibitors.

SUMMARY OF THE INVENTION

An object of the present invention is to provide novel alpha substituted oxo- or thio-trifluoromethylketone compounds which inhibit cytosolic phopholipase A2 enzymes that are pro-inflammatory mediators. Some of the derivatives covered by the present invention exhibit increased stability and aqueous solubility.

This invention relates to a novel compound of the formula

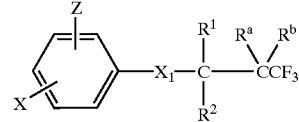
I wherein:

$X_1$ is O or S(O)$_n$;

n is 0, 1 or 2;

$R^a$ and $R^b$ when taken together form an oxo (=O) group, or $R^a$ and $R^b$ are each independently hydrogen or OH;

X is H, CF$_3$, halogen, NR$^3$R$^4$, NH(CO)NHR$^3$R$^4$, C(O)NR$^3$R$^4$, OH, OR$^8$, SH, S(O)$_n$R$^8$, C(O)OR$^6$, NH(CO)OR$^8$, C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being optionally substituted by COOR$^6$, CN, C(O)NR$^3$R$^4$, PO$_3$R$^6$, SO$_3$R$^6$, heterocyclic, OH, OR$^8$, SH, S(O)$_n$R$^8$, NR$^3$R$^4$, NH(CO)NR$^3$R$^4$, NH(CO)OR$^8$, OC(O)OR$^8$, aryl or heteroaryl, said aryl or heteroaryl being optionally substituted by one or two groups independently selected from COOR$^6$, SO$_3$R$^6$, OCOR6, PO$_3$R$^6$ or heterocyclic;

$R^1$ and $R^2$ are each independently H, substituted C$_1$–C$_7$ alkyl, C$_2$–C$_7$ alkenyl, C$_2$–C$_7$ alkynyl or C$_3$–C$_7$ cycloalkyl, said alkyl group being substituted by, and said alkenyl, alkynyl or cycloalkyl group being optionally substituted by, COOR$^6$, CN, C(O)NR$^3$R$^4$, PO$_3$R$^6$, SO$_3$R$^6$, heterocyclic, OH, OR$^8$, SH, S(O)$_n$R$^8$, NR$^3$R$^4$, NH(CO)NR$^3$R$^4$, NH(CO)OR$^8$, OC(O)OR$^8$, aryl or heteroaryl, said aryl or heteroaryl group being optionally substituted by one or two groups independently selected from COOR$^6$, SO$_3$R$^6$, PO$_3$R$^6$ or heterocyclic;

$R^3$ and $R^4$ are each independently H, C$_1$–C$_7$ alkyl, C$_2$–C$_7$ alkenyl, C$_2$–C$_7$ alkynyl, C$_3$–C$_7$ cycloalkyl, heterocyclic or aryl, said alkyl, alkenyl, alkynyl, cycloalkyl, heterocyclic or aryl group being optionally substituted with COOR$^6$, CN, OR$^6$, NR$^6$R$^7$, SO$_3$R$^6$, PO$_3$R$^6$, halogen, aryl or heteroaryl, said aryl or heteroaryl substituent being optionally substituted with one or two groups independently selected from COOR$^6$, SO$_3$R$^6$, PO$_3$R$^6$ or heterocyclic;

$R^5$ is H, C$_1$–C$_7$ alkyl or C$_3$–C$_7$ cycloalkyl, said alkyl or cycloalkyl group being optionally substituted by COOR$^6$, CN, C(O)NR$^3$R$^4$, PO$_3$R$^6$, SO$_3$R$^6$, heterocyclic, OR$^3$, S(O)$_n$R$^8$, NR$^3$R$^4$, NH(CO)NR$^3$R$^4$, NH(CO)OR$^8$, C(O)$_2$OR$^8$, aryl or heteroaryl, said aryl or heteroaryl group being optionally substituted by one or two groups independently selected from COOR$^6$, SO$_3$R$^6$, PO$_3$R$^6$ or heterocyclic;

$R^6$ and $R^7$ are independently H, C$_1$–C$_7$ alkyl or C$_3$–C$_7$ cycloalkyl;

$R^8$ is the same as $R^3$ but cannot be H;

Z is OR$^9$, S(O)$_n$R$^9$, NR$^9$R$^{10}$ or CHR$^9$R$^{10}$;

$R^9$ and $R^{10}$ are each independently hydrogen, C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being optionally substituted with NR$^{11}$R$^{12}$, SR$^{11}$, S(O)R$^{16}$, SO$_2$R$^{16}$ or OR$^{11}$, with the proviso that both $R^9$ and $R^{10}$ may not both be hydrogen;

$R^{11}$ and $R^{12}$ are each independently H, C$_1$–C$_7$ alkyl, C$_2$–C$_7$ alkenyl, C$_2$–C$_7$ alkynyl, C$_3$–C$_7$ cycloalkyl or aryl, said alkyl, alkenyl, alkynyl, cycloalkyl or aryl group being optionally substituted by 1–3 $COOR^6$, $OR^6$, $SiR^{13}R^{14}R^{15}$, $OR^{13}$, aryl, biaryl or heteroaryl, said aryl, biaryl or heteroaryl group being optionally substituted with 1–3 halogen, $CF_3$, $OR^6$, $COOR^6$, $NO_2$ or CN, or $R^{11}$ and $R^{12}$ taken together with the nitrogen to which they are attached form a 5–7 membered heterocyclic ring with one or more O, N or S heteroatoms, said heterocyclic ring being optionally substituted with $COOR^6$ or $C_1$–$C_5$ alkyl optionally substituted with $OR^6$, $COOR^6$ or $C(O)NR^3R^4$; and $R^{13}$, $R^{14}$ and $R^{15}$ are each independently aryl, benzyl, benzhydryl, biaryl, heteroaryl, aryl($C_1$–$C_6$)alkyl or heteroaryl($C_1$–$C_6$)alkyl, said aryl group being optionally substituted with halogen, $CF_3$, $OR^6$, $COOR^6$, $NO_2$, CN or $C_1$–$C_7$ alkyl;

$R^{16}$ is the same as $R^{11}$ and $R^{12}$ but is not hydrogen; or a pharmaceutically acceptable salt thereof, with the proviso that $R^1$ and $R^2$ may not both be hydrogen.

Another aspect of this invention involves methods for inhibiting cytosolic $PLA_2$ in a mammal in need thereof which comprises administering to said mammal a therapeutically effective amount of a compound of formula I and methods for using the compounds of formula I to treat various diseases characterized by inappropriate activation of the cytosolic $PLA_2$ enzymes such as asthma, allergic rhinitis, cerebral ischemia, Alzheimer's Disease, rheumatoid arthritis, acute pancreatitis, inflammatory bowel disease, psoriasis, gout, neutrophil and platelet activation, chronic skin inflammation, shock, trauma-induced inflammation such as spinal cord injury, damage to the skin resulting from UV light or burns and macrophage activation. In further aspects, the present invention provides pharmaceutical compositions comprising a therapeutically effective amount of a compound of formula I and a pharmaceutically acceptable carrier and processes for preparing the compounds of formula I.

DETAILED DESCRIPTION

The object of this invention was to discover a selective $cPLA_2$ inhibitor which is active, both topically and orally, in treating inflammary disease of the skin and other tissues as well as other chronic and acute conditions which have been linked to inappropriate activation of the $cPLA_2$ enzymes. Preferably such compound would also be devoid of undesirable lipid-perturbing activities associated with skin irritation.

The above-mentioned objectives have been met by the compounds of formula I described above.

In the present application the numbers in the subscript after the symbol "C" define the number of carbon atoms a particular group can contain. For example, "$C_1$–$C_7$ alkyl" refers to straight and branched chain alkyl groups with 1 to 7 carbon atoms. Similarly, "$C_2$–$C_7$ alkenyl" refers to an unsaturated hydrocarbon group containing from 2 to 7 carbon atoms and at least one carbon-carbon double bond. The term "$C_2$–$C_7$ alkynyl" refers to an unsaturated hydrocarbon group containing from 2 to 7 carbon atoms and at least one carbon-carbon triple bond.

The term "halogen" or "halo" as used herein refers to fluorine, chlorine, bromine or iodine.

"Aryl" as used herein refers to a $C_6$ monocyclic aromatic ring system or a $C_9$ or $C_{10}$ bicyclic carbocyclic ring system having one or two aromatic rings such as phenyl or naphthyl. It may also refer to a $C_{14}$ tricyclic carbocyclic ring system having two or three aromatic rings such as anthracenyl or phenanthrenyl. Unless otherwise indicated, "substituted aryl" refers to aryl groups substituted with one or more (preferably from 1 to 3) substituents independently selected from ($C_1$–$C_6$)alkyl, halo($C_1$–$C_6$)alkyl, ($C_1$–$C_6$)alkoxy, ($C_1$–$C_6$)alkoxy-carbonyl, ($C_1$–$C_6$)alkanoyl, hydroxy, halo, mercapto, nitro, amino, cyano, ($C_1$–$C_6$)alkylamino, di($C_1$–$C_6$)alkylamino, carboxy, aryl, aryl ($C_1$–$C_6$)alkyl, aryl ($C_1$–$C_6$)alkoxy, heterocyclic, heterocyclic ($C_1$–$C_6$)alkyl and the like. The term "biaryl" refers to two $C_6$ monocyclic aromatic ring systems or two $C_9$ or $C_{10}$ bicyclic carbocyclic ring systems linked together such as o-, m- and p-biphenyl or o-, m- and p-binaphthyl. The term "heteroaryl" refers to a 5- or 6-membered aromatic ring system or a 9- or 10-membered bicyclic aromatic ring system containing one, two or three heteroatoms selected from N, O and S. The term "benzhydryl" refers to a carbon atom bearing two aryl, bis-aryl or heteroaryl groups.

The term "heterocyclic" as used herein refers to a 4—, 5- or 6-membered ring containing one, two or three heteroatoms selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic" also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolidinyl, pyridyl, piperidyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, benzimidazolyl, benzothiazolyl, benzoxazolyl, benzofuranyl, furyl, dihydrofuranyl, tetrahydrofuranyl, pyranyl, dihydropyranyl, dioxolanyl, thienyl, benzothienyl and diaxanyl.

In a preferred embodiment the compounds of general formula I have $R^1$ being hydrogen.

In another preferred embodiment the compounds of general formula I have X being hydrogen.

Another preferred embodiment embraces the compounds of formula I wherein X is hydrogen, $R^1$ is hydrogen and $R^2$ is $C_1$–$C_7$ alkyl substituted by COOH or $C_1$–$C_7$ alkyl substituted by carboxy-substituted phenyl.

Still another preferred embodiment includes the compounds of formula I wherein Z is Y—$Z^1$;

$$Y \text{ is } -O-, \quad -S(O)_{\overline{n}}-, \quad -\overset{R^c}{\underset{|}{N}}- \text{ or } -CH_2;$$

$R^c$ is H, —COCF$_3$, —COC$_6$H$_5$, —COO(C$_1$–C$_6$)alkyl,

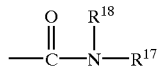

in which $R^{18}$ and $R^{17}$ are each independently H or (C$_1$–C$_6$)alkyl, (C$_1$–C$_{18}$)alkyl or (C$_1$–C$_{18}$)alkyl substituted by one or more of phenyl or phenyl substituted by 1–5 fluoro, 1–3 halo (other than fluoro), 1–3 (C$_1$–C$_6$) alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$) alkylamino, 1–3 carboxyl, 1–3 —COO(C$_1$–C$_6$)alkyl, 1–3 —SO$_3$H, 1–3 —SO$_2$NHR$^{19}$ in which $R^{19}$ is H or (C$_1$–C$_6$)alkyl, or 1–3 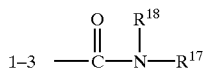

in which $R^{18}$ and $R^{17}$ are as defined above;

$Z^1$ is (a)

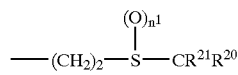

in which $n^1$ is 0, 1 or 2 and $R^{21}$ and $R^{20}$ are phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$)alkylamino, 1–3 carboxy, 1–3 —COO(C$_1$–C$_6$)alkyl, 1–3 —SO$_3$H, 1–3 —SO$_2$NHR$^{19}$ in which $R^{19}$ is as defined above, or 1–3 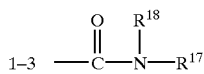

in which $R^{18}$ and $R^{17}$ are as defined above;

(b)

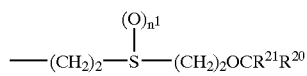

in which $n^1$ is 0, 1 or 2 and $R^{21}$ and $R^{20}$ are as defined above;

(c)

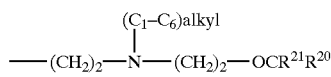

in which $R^{21}$ and $R^{20}$ are as defined above;

(d)

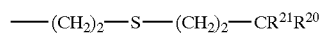

in which $R^{21}$ and $R^{20}$ are as defined above;

(e)

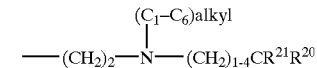

in which $R^{21}$ and $R^{20}$ are as defined above; or (f)

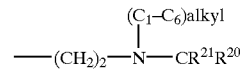

in which $R^{21}$ and $R^{20}$ are as defined above.

A most preferred embodiment is a compound of the formula

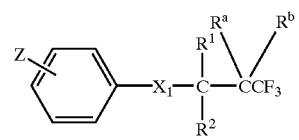

wherein X, is O or S(O)$_n$;

n is 0, 1 or 2;

$R^a$ and $R^b$ when taken together form an oxo (=O) group, or $R^a$ and $R^b$ are each independently hydrogen or OH;

$R^1$ is hydrogen;

$R^2$ is C$_1$–C$_7$ alkyl substituted by COOH or C$_1$–C$_7$ alkyl substituted by carboxy-substituted phenyl;

Z is Y—Z$^1$;

Y is —CH$_2$; and $Z^1$ is 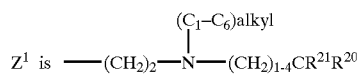

in which $R^{20}$ and $R^{21}$ are phenyl substituted by 1–3 halo; or a pharmaceutically acceptable salt thereof.

Some of the compounds described herein contain one or more asymmetric centers and may thus give rise to diastereomers and optical isomers. The present invention is meant to include such possible diastereomers as well as their racemic and resolved, enantiomerically pure forms, and pharmaceutically acceptable salts thereof.

As mentioned above the invention also includes pharmaceutically acceptable salts of the compounds of formula I. A compound of the invention can possess a sufficiently acidic, a sufficiently basic, or both functional groups. Accordingly, a compound may react with any of a number of inorganic bases, and organic and inorganic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylene-sulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Suitable organic bases include trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine, or the like pharmaceutically acceptable amines. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

The present invention also includes solvated forms of the compounds of formula I, particularly hydrates, in which the trifluoromethyl ketone group exists as a mixture of ketonic I and hydrated forms II and are each independently interconvertible and pharmacologically active.

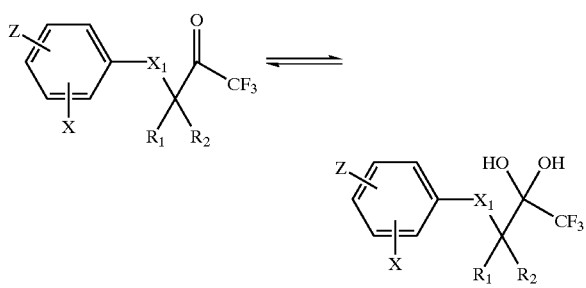

Biological Activity

The assay determining the activity as cPLA$_2$ inhibitors is the following:

$^3$H-arachidonate-labeled U937 membranes were prepared from U937 cells grown in RPMI 1640 medium containing L-glutamine supplemented with 10% fetal calf serum and 50 μg/ml gentamycin in a 5% CO$_2$ incubator at 37° C. Sixteen hours prior to harvesting the cells, $^3$H-arachidonate (100 Ci/mmol) was added to the cell culture (1×10$^6$ cells/ml, 0.5 μCi/ml). After washing the cells with HBSS (Hank's Balanced Salts) containing 1 mg/ml HSA (Human Serum Albumin), the cells were lysed by nitrogen cavitation and the homogenate was centrifuged at 2,000×g for 10 minutes. The supernatant was further centrifuged at 50,000×g for 30 minutes after which the pellet was resuspended in water and autoclaved at 120° C. for 15 minutes to inactivate any residual phospholipase A$_2$ activity. This suspension was then recentrifuged at 50,000×g for 30 minutes and the pellet resuspended in distilled water.

Assays of cPLA$_2$ activity using these $^3$H-arachidonate-labeled U937 membranes as substrate typically employ human recombinant cPLA$_2$ [see Burke et al., *Biochemistry*, 1995, 34: 15165–15174] and membrane substrate (22 μM phospholipid) in 20 mM HEPES [N-(2-hydroxyethyl) piperazine-N$^1$-(2-ethanesulfonic acid)] buffer, pH 8, containing 6 mM CaCl$_2$, 0.9 mg/ml albumin and 4 M glycerol. Enzyme assays are allowed to proceed for 3 hours at 37° C. before removing the non-hydrolyzed membranes. The hydrolyzed, radiolabeled fatty acid is then measured by liquid scintillation counting of the aqueous phase.

The effects of inhibitor are calculated as percent inhibition of $^3$H-arachidonate formation, after correcting for nonenzymatic hydrolysis, as compared to a control lacking inhibitor according to the following formula:

percent inhibition=((Control DPM−Inhibitor DPM)/Control DPM)×100%

Various concentrations of an inhibitor were tested, and the percent inhibition at each concentration was plotted as log concentration (abscissa) versus percent inhibition (ordinate) to determine the IC$_{50}$ values.

In this assay the compounds of Examples 1 shown below exhibited cPLA$_2$ IC$_{50}$ values in the range of from about 1 to 50 μM.

Since the compounds of the present invention are selective inhibitors of cytosolic phospholipase A$_2$, they are of value in the treatment of a wide variety of clinical conditions.

Inflammatory disorders which may be treated by inhibition of cytosolic cPLA$_2$ include such conditions as arthritis, psoriasis, asthma, inflammatory bowel disease, gout, trauma-induced inflammation such as spinal cord injury, Alzheimer's Disease, cerebral ischemia, chronic skin inflammation, shock, damage to skin resulting from exposure to ultraviolet light or burns, allergic rhinitis, acute pancreatitis, and the like.

The compounds of the present invention have also been found to be very stable towards keto-reduction. It has been shown that a reliable method to assess keto-stability of compounds is to measure the percent of such compounds remaining after incubation with erythrocyte lysates [Rady-Pentek P., et al., *Eur. J. Clin. Pharmacol.*, 1997, 52(2): 147–153]. The assay is the following.

Male Wistar rates were anesthetized with CO$_2$ and then blood was removed by direct cardio-puncture or through a pre-inserted jugular vein canula into syringes that were pre-rinsed with heparin. The blood was then inserted into heparanized tubes and placed on ice. The blood was centrifuges as 3000 rpm for 5 minutes to separate the plasma. The plasma was removed and an equivalent volume of sterile water was mixed with the erythrocyte fraction. This was mixed by inversion and left on ice for several minutes to lyse the erythrocytes. The erythrocyte-water mixture was then centrifuged at 3000 rpm for 5 minutes to pellet the cellular debris.

Each compound was dissolved in methanol (1 ml) to produce a 2 mM solution. From this solution, 50 µl aliquot was made up to 1 ml in 50% methanol to produce a 100 µM stock solution. From this solution, a dose solution was prepared by diluting 100 µl to 2 ml of a 0.1 M potassium phosphate buffer (pH=7.4) to produce a 2 µM final incubation dilution.

The lysate (250 µl) was then aliquoted into eppendorf tubes, 6 for each compound, i.e. 0 time, 15 minutes, 60 minutes in duplicate. To these aliquots was added 200 µl of the dose solution and this was preheated to 37° C. for 2–3 minutes prior to the addition of NADPH (1 mM final concentration) to start the reactions. The reactions were terminated with the addition of either 0.5 ml or 1 ml of acetonitrile. Following centrifugation at 8000×g for 5 minutes, the supernatant was removed and stored at −20° C. until analysis could proceed by quantitative LC/MS. Samples were analyzed by electrospray ionization (ESI) on a Micromass ZMD 2000® single quadrupole mass spectrometer coupled to a Shimadzu HPLC system. The percent of compound remaining following 15 minutes and 60 minutes incubation is calculated relative to the 0 time point.

Administration Modes

The compounds of formula I are usually administered in the form of pharmaceutical compositions. They can be administered by a variety of routes including oral, rectal, transdermal, subcutaneous, intravenous, intramuscular, and intranasal. The compounds are effective as both injectable and oral compositions. Such compositions are prepared in a manner well known in the pharmaceutical art and comprise at least one active compound defined by formula I and a pharmaceutically acceptable carrier.

In making the compositions employed in the present invention the active ingredient is usually mixed with an excipient, diluted by an excipient or enclosed within a carrier which can be in the form of a capsule, sachet, paper or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Method of Preparation

The compounds of the present invention can be prepared by various methods which are known in the art. Illustrative methods of preparation are provided in the reaction scheme which follows and in the Examples.

Preparation of compounds of formula I may be accomplished via the synthetic scheme which is described below. The specific examples which follow illustrate the synthesis of representative compounds of the present invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

Scheme A

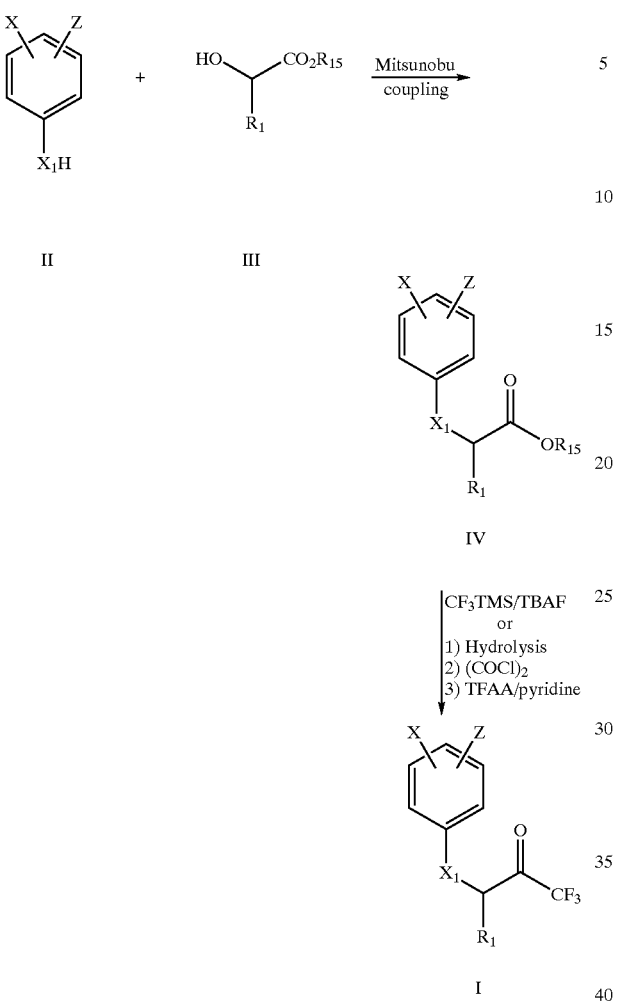

Scheme A describes a method to prepare the various α-substituted thio- and oxo-trifluoromethylketones of generic structure I. Thus, the various phenols or thiophenols of type II may be reacted under Mitsunobu conditions with the various lactic acids or esters III to give the compounds of generic formula IV. Subsequent conversion to the trifluoromethylketone analogs I may be performed by hydrolysis of the esters to the corresponding acids followed by conversion to the acid chloride and treatment with trifluoroacetic anhydride or by direct conversion of the esters using trifluorotrimethylsilane.

SPECIFIC EXAMPLES

The following examples further illustrate the preparation of the compounds of formula I. The examples are illustrative only and are not intended to limit the scope of the invention in any way. The following abbreviations have the indicated meanings:

| | |
|---|---|
| AcOH | acetic acid |
| EWG | electron-withdrawing groups |
| DIAD | diisopropyl azodicarboxylate |
| TFAA | trifluoroacetic anhydride |
| THF | tetrahydrofuran |
| TFA | trifluoroacetic acid |
| EEDQ | N-ethoxycarbonyl-2-ethoxy-1,2-dihydroxyquinoline |
| DMF | N,N-dimethylformamide |
| DEAD | diethyl azodicarboxylate |
| CPBA | m-chloroperbenzoic acid |
| Me | $CH_3$ |
| Ph | phenyl |
| tBu | tert-butyl |
| TBAF | tetrabutylammonium fluoride |
| CF3TMS | trifluoromethyltrimethylsilane |

Analytical grade solvents were used for reactions and chromatographies. Flash column chromatographies were performed on Merck silica gel 60 (230–400 Mesh) and Merck silica gel 60 $F_{254}$ 0.5 mm plates were used. All melting points were determined on a Gallenkamp melting point apparatus and were not corrected. $^1H$ NMR spectra were measured on a Bruker AMX400 (400 MHz) instruments. Chemical shifts were reported in δ units using the solvent as internal standard. The signals are described as s (singlet), d (doublet), t (triplet), qa (quartet), qi (quintet), m (multiplet) and br (broad). Infrared spectras were recorded on a Perkin-Elmer 781 and optical rotations were measured on a Perkin-Elmer 241 apparatus.

Example 1

3-[4-[3-[N-[2-Bis-(4-chlorophenyl)ethyl]-N-methylamino]propyl]phenoxy]-3-(5-carboxypentyl)-1,1,1-trifluoro-2-propanone, Trifluoroacetic Acid Salt

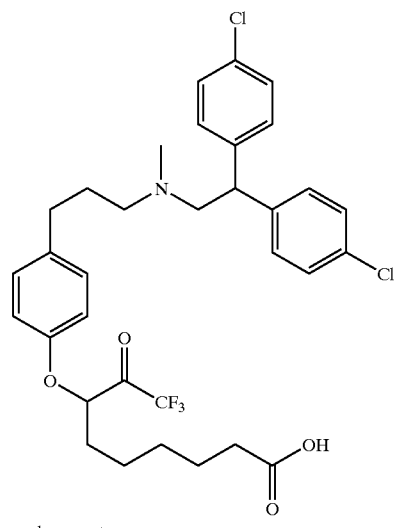

t-Butyl 6-bromohexanoate

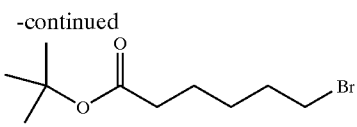

To a mixture of 1,4-dioxane (70 ml) and concentrated sulfuric acid (7 ml) in a pressure bottle was added 6-bromohexanoic acid (10 g, 46.9 mmol). iso-Butene (60 ml) was then introduced to the above solution at 0° C. The resulting mixture was stirred at room temperature for 2 days, cooled to 0° C. and poured slowly into an aqueous solution (200 ml) of sodium bicarbonate (20 g). The mixture was stirred at room temperature for 15 minutes and extracted with diethyl ether. The organic phase was washed three times with brine, dried over sodium sulfate and concentrated in vacuo. The residue was distillated to give the title compound (6 g, 51%) as a colorless liquid (90–95° C./1 mmHg).

Methyl 7-tert-Butoxycarbonyl-2-oxoheptanoate

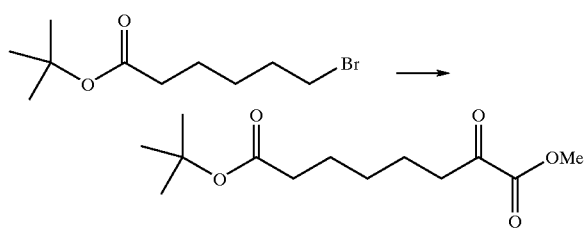

To a suspension of activated zinc (0.65 g, 10 mmol) in THF (20 ml) was added t-butyl 6-bromohexanoate (1.38 g, 5.5 mmol). The mixture was stirred at room temperature for 15 hours. The excess zinc was allowed to settle for 2 hours. The solution was then transferred to a pre-formed solution of CuCN (0.45 g, 10.7 mmol) and LiCl (0.45 g, 10.7 mmol) at −20° C. The resulting mixture was stirred at 0° C. for 5 minutes and cooled to −60° C., and methyl chlorooxoacetate (0.68 ml, 5.5 mmol) was added. The resulting mixture was stirred at −60° C. for 1 hour, and reaction temperature allowed to rise gradually to 0° C. over 4 hours. The mixture was then poured into aqueous ammonium chloride, extracted 3 times with ether. The combined organic phase was washed with aqueous ammonium chloride, brine, dried over sodium sulfate and concentrated in vacuo to afford the title material (1.1 g) as a pale yellow liquid, which is used directly in next step.

Methyl 7-tert-Butoxycarbonyl-2-hydroxyheptanoate

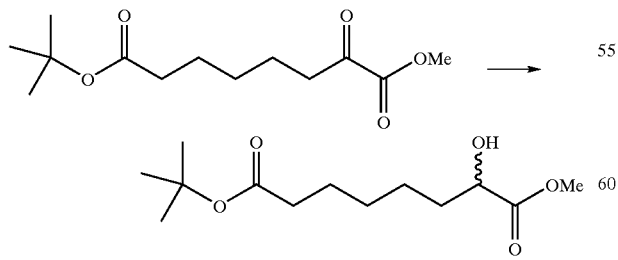

A solution of crude methyl 7-tert-butoxycarbonyl-2-oxoheptanoate (1 g) in 1,2-dichloroethane (10 ml) was treated with sodium triacetoxyborohydride (822 mg, 3.88 mmol). The mixture was stirred at room temperature for 16 hours, quenched with sat. aq. sodium bicarbonate and extracted with ether. The organic phase was washed with aq. sodium bicarbonate, brine, dried over sodium sulfate and concentrated in vacuo. The residue was chromatographed on silica gel (hexane:ethyl acetate=4:1) to give the title compound (554 mg, 43%, 2 steps) as a colorless liquid.

3-(4-Tert-butyldimethylsilyloxy-phenyl)-1-methanesulfonyloxy-propane

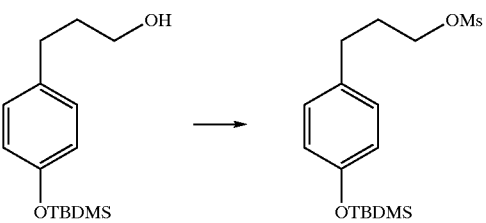

A solution of 3-(4-tert-butyldimethylsilyloxy-phenyl)-1-propanol (P. A. Grieco and C. J. Markworth, *Tet. Lett.*, 1999, 40: 665) (2.86 g, 10.73 mmol) in dry dichloromethane (25 ml), was cooled to 0–5° C. and treated with triethylamine (2.4 ml, 17.0 mmol). Then methanesulfonyl chloride (1.08 ml, 14 mmol) was added dropwise over 10 minutes. The reaction mixture was stirred at 0–5° C. for 1 hour, then quenched with sat. sodium bicarbonate, diluted with ethyl acetate (300 mL), washed with water, brine, dried over anhydrous magnesium sulfate, filtered and concentrated. The residue was filtered aon a silica gel pad (toluene/ethyl acetate 95:5) to give the title material (3.68 g, 100%) as a clear oil.

$^1$H NMR (CDCl$_3$, δ, ppm): 0.198 (6H, s, 2×—CH$_3$), 0.99 (9H, s, -tBu), 2.04–2.07 (2H, m, —CH$_2$—), 2.69 (2H, t, J=7.3 Hz, Ar—CH$_2$—), 2.99 (3H, s, —SO$_2$Me), 4.23 (2H, t, J=6.4 Hz, —CH$_2$O—), 6.78 (2H, d, J=8.5 Hz, aromatic H), 7.04 (2H, d, J=8.3 Hz, aromatic H). Anal. Calcd. for C$_{16}$H$_{28}$O$_4$SSi: C, 55.78; H, 8.19. Found: C, 55.92; H, 8.16.

4-[3-[N-[2-bis-(4-Chlorophenyl)ethyl]-N-methylamino]propyl]-tertbutyidimethylsilyloxybenzene

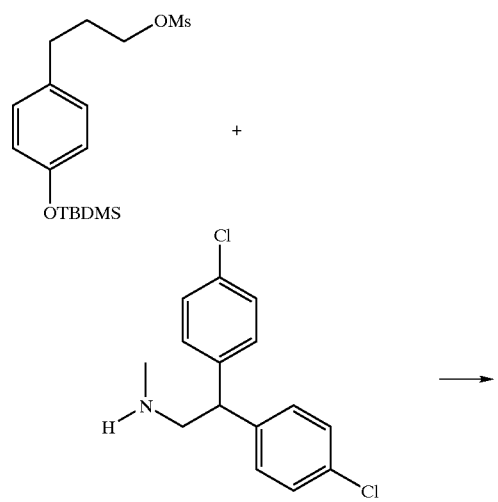

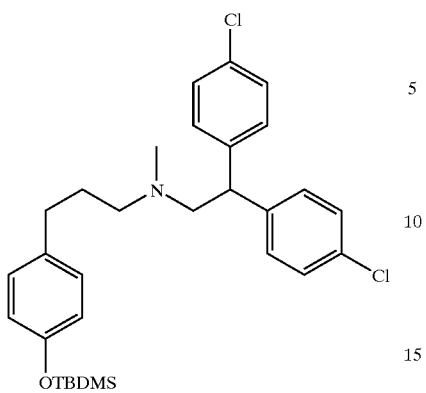

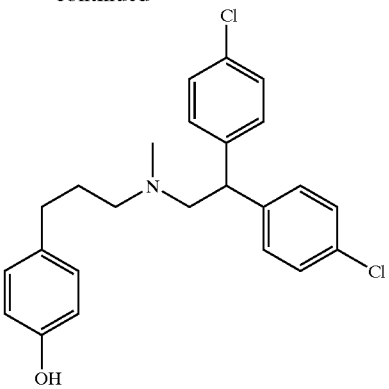

A solution of 3-(4-tert-butyidimethylsilyloxy-phenyl)-1-methanesulfonyloxy-propane (3.60 g, 10.45 mmol) in acetonitrile (30 ml) was treated with N-methyl-2-bis-(4-chlorophenyl)ethylamine (B. E. Maryanoff, S. O. Nortey and J. F. Gardocki, *J. Med. Chem.*, 1984, 27: 1067) (3.07 g, 10.97 mmol) and N,N-diisopropylethylamine (2.73 ml, 15.67 mmol). Then potassium iodide (0.14 g) was added and the mixture was heated under reflux for 18 hours. The mixture was diluted with ethyl acetate, washed with 5% aq. sodium carbonate, brine, dried over anhydrous magnesium sulfate, filtered and concentrated. The residual orange oil was purified by silica gel chromatography (toluene/ethyl acetate 95:5) to give the title material (5.18 g, 94%).

$^1$H NMR (CDCl$_3$, δ, ppm): 0.19 (6H, s, 2×—CH$_3$), 0.99 (9H, s, -tBu), 2.25 (3H, br s, —NCH$_3$), 2.37–2.46 (4H, m, 2×—NCH$_2$—), 2.87 (2H, br s, —CH$_2$O—), 4.05 (1H, br s, —CH(Ar)$_2$), 6.75 and 6.94 (2×2H, 2 d, J=8.4 Hz, aromatic H), 7.14 and 7.26 (2×4H, 2 d, J=8.5 Hz, aromatic H). Anal. Calcd. for C$_{30}$H$_{39}$Cl$_2$NOSi: C, 68.16; H, 7.44. Found: C, 68.22; H, 7.41. MS (ESI): 528 (M+H)$^+$.

4-[3-[N-[2-bis-(4-Chlorophenyl)ethyl]-N-methylamino]propyl]phenol

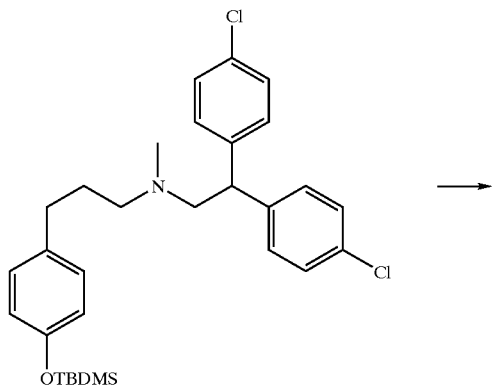

A solution of 4-[3-[N-[2-bis-(4-chlorophenyl)ethyl]-N-methylamino]propyl]-tertbutyldimethylsilyloxybenzene (1.90 g, 3.59 mmol) in tetrahydrofuran ((20 ml) was treated with acetic acid (1.2 ml, 21.5 mmol) followed by tetrabutylammonium fluoride (1M in tetrahydrofuran, 10.8 ml, 10.8 mmol). The resulting mixture was stirred at 22° C. for 2 hours. The mixture was diluted with ethyl acetate, washed with sat. sodium bicarbonate, brine, dried over anhydrous magnesium sulfate, filtered and concentrated. The residual oil was purified by silica gel chromatography (toluene/ethyl acetate 8:2 to 7:3) and gave the title material (1.50 g, 100%) as an oil.

$^1$H NMR (DMSO-d$_6$, δ, ppm): 1.54 (2H, m, —CH$_2$—), 2.15 (3H, s, —NCH$_3$), 2.25–2.32 (4H, m, ArCH$_2$— and —CH$_2$N—), 2.84 (2H, d, J=8.0 Hz, —NC$\underline{H}_2$—CH—), 4.23 (1H, t, J=8.0 Hz, —CH(Ar)$_2$), 6.62 (2H, d, J=8.4 Hz, aromatic H), 6.85 (2H, d, J=8.4 Hz, aromatic H), 7.30 (8H, s, aromatic H). Anal. Calcd. for C$_{24}$H$_{25}$Cl$_2$NO. HCl: C, 61.96; H, 5.98; N, 3.01. Found: C, 61.99; H, 5.85; N, 3.06. MS (ESI): 414 (M+H)$^+$.

Methyl 2-[4-[3-[N-[2-bis-(4-Chlorophenyl)ethyl]-N-methylamino]propyl]phenoxy]-2-(5-tert-butyloxycarbonylpentyl)-ethanoate

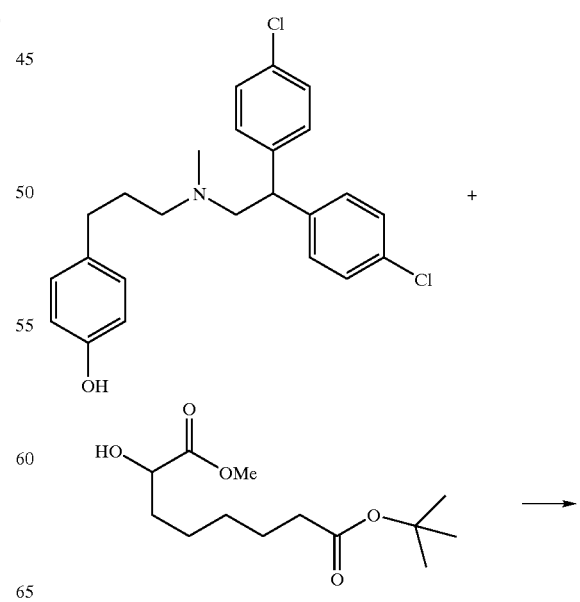

29
-continued

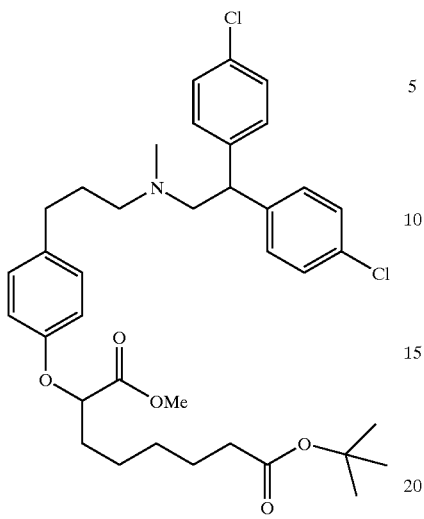

30
-continued

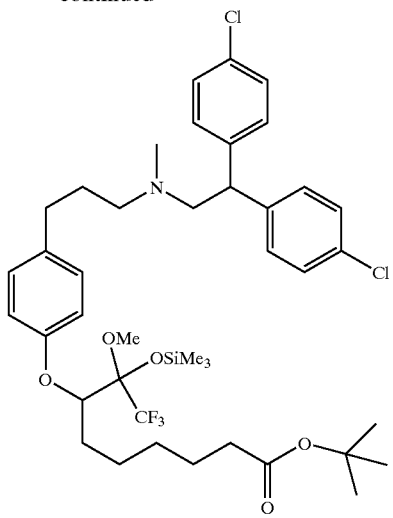

To a solution of 4-[3-[N-[2-bis-(4-chlorophenyl)ethyl]-N-methylamino]propyl]phenol (182 mg, 0.439 mmol), methyl 7-tert-butoxycarbonyl-2-hydroxyheptanoate (114 mg 0.439 mmol) and triphenyl phospine (127 mg, 0.483 mmol) in THF (2 ml) was added dropwise diethyl azodicarboxylate (76 μl, 0.483 mmol). The mixture was stirred at room temperature for 16 hours and concentrated in vacuo. The residue was chromatographed on silica gel (hexane:ethyl acetate:triethylamine=18:1:1) to give the title compound (162 mg, 56%) as a colorless oil.

3-[4-[3-[N-[2-Bis-(4-chlorophenyl)ethyl]-N-methylamino] propyl]phenoxy]-3-(5-tert-butyloxycarbonylpentyl)-2-methoxy-2-trimethylsilyloxy-1,1,1-trifluoropropane A solution of methyl 2-[4-[3-[N-[2-bis-(4-chlorophenyl) ethyl]-N-methylamino]propyl]phenoxy]-2-(5-tert-butyloxycarbonylpentyl)-ethanoate (103 mg, 0.157 mmol) and trifluoromethyltrimethylsilane (210 μl, 1.4 mmol) in toluene (1 ml) at −78° C. was treated with tetrabutyl ammonium fluoride (1.0 M in THF, 8 μl, 0.008 mmol). The cooling bath was removed, and reaction mixture was stirred at room temperature for 0.5 hours and concentrated in vacuo. The residue was chromatographed on silica gel (hexane:ethyl acetate=1:0 to 5:1) to give the title compound (80 mg, 64%) as a pale yellow oil.

3-[4-[3-[N-[2-Bis-(4-chlorophenyl)ethyl]-N-methylamino] propyl]phenoxy]-3-(5-tert-butyloxycarbonylpentyl)-1,1,1-trifluoro-2-propanone

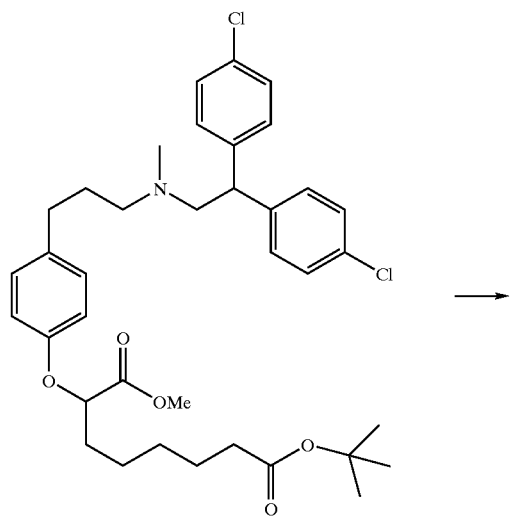 →

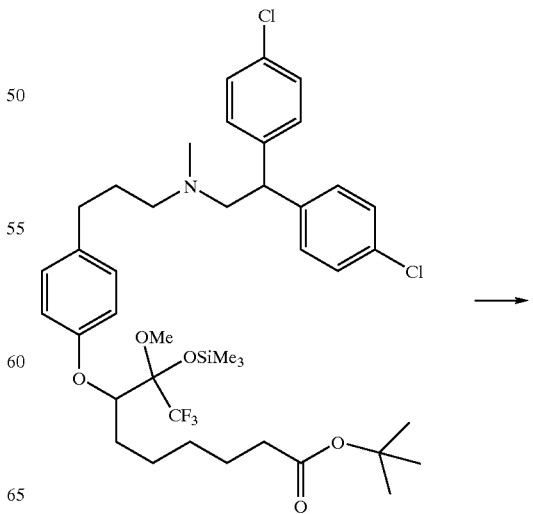 →

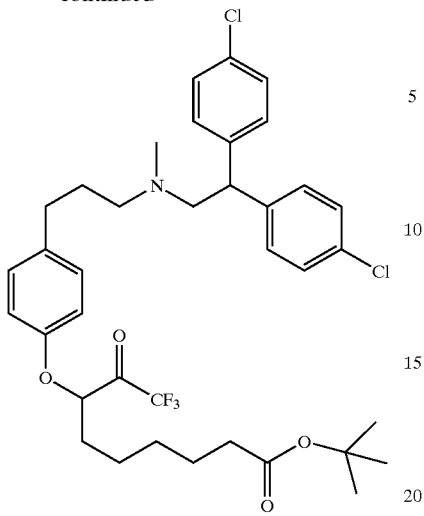

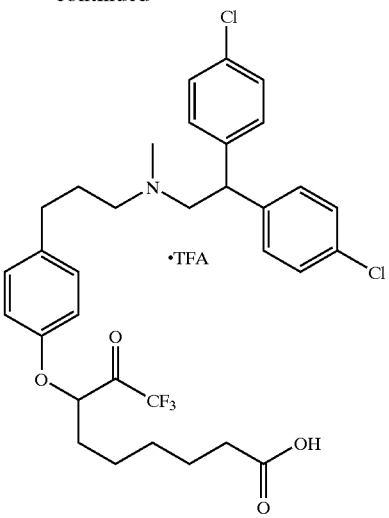

A solution of 3-[4-[3-[N-[2-Bis-(4-chlorophenyl)ethyl]-N-methylamino]propyl]phenoxy]-3-(5-tert-butyloxycarbonylpentyl)-2-methoxy-2-trimethylsilyloxy-1,1,1-trifluoropropane (52 mg, 0.065 mmol) in THF (1 ml) was treated with a mixture of tetrabutylammonium fluoride and acetic acid (1.0M in THF, 79 μl, 0.079 mmol). The mixture was stirred at room temperature for 10 minutes, diluted with ethyl acetate, washed with sat. aq. sodium bicarbonate, brine, dried over sodium sulfate and concentrated in vacuo. The residue was chromatographed on silica gel (hexane:ethyl acetate=2:1) to give the title compound (43 mg, 95%) as a colorless oil.

Treatment of the above free amine with anhydrous hydrogen chloride (1.0 M in ether) gave the hydrochloride salt as a colorless syrup.

3-[4-[3-[N-[2-Bis-(4-chlorophenyl)ethyl]-N-methylamino] propyl]phenoxy]-3-(5-carboxypentyl)-1,1,1-trifluoro-2-propanone, Trifluoroacetic Acid Salt

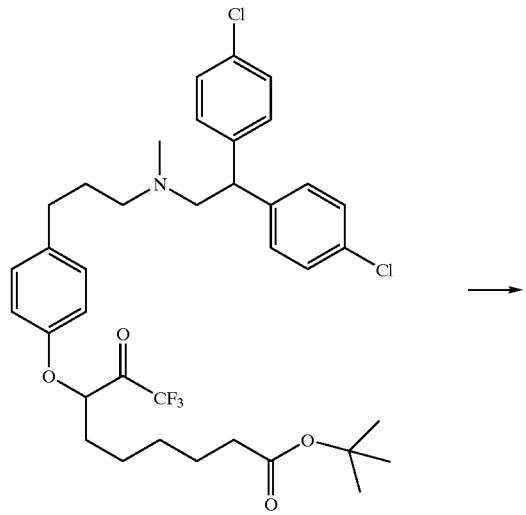

A solution of 3-[4-[3-[N-[2-Bis-(4-chlorophenyl)ethyl]-N-methylamino]propyl]phenoxy]-3-(5-tert-butyloxycarbonylpentyl)-1,1,1-trifluoro-2-propanone (32 mg, 0.046 mmol) in dichloromethane (1 ml) was treated with trifluoroacetic acid (0.2 ml). The mixture was stirred at room temperature for 1 hour and concentrated in vacuo to give the trifluoroacetic acid salt of the title compound as a colorless syrup.

Example 2

3-[4-[3-[N-[2-Bis-(4-Chlorophenyl)ethyl]-N-methylamino]propyl]phenoxy]-3-(3-carboxypropyl)-1,1,1-trifluoro-2-propanone, Trifluoroacetic Acid Salt

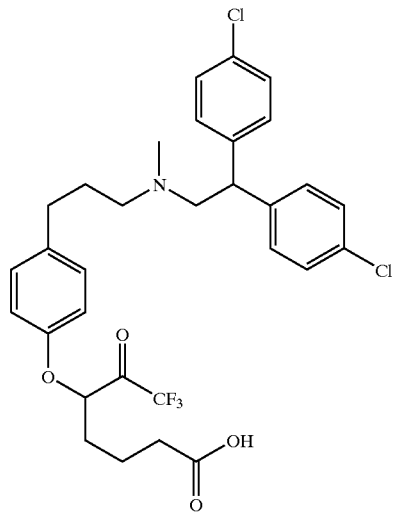

t-Butyl 4-Bromobutanoate

4-Bromobutanoic acid (8 g, 47.9 mmol) and iso-butene (60 ml) were reacted by the same procedure as described in Example 1 for the preparation of tert-butyl 6-bromohexanoate to give the title material (5.7 g, 54%) as a colorless liquid (b.p. 62–64° C./10 mmHg).

Methyl 5-tert-Butoxycarbonyl-2-oxopentanoate

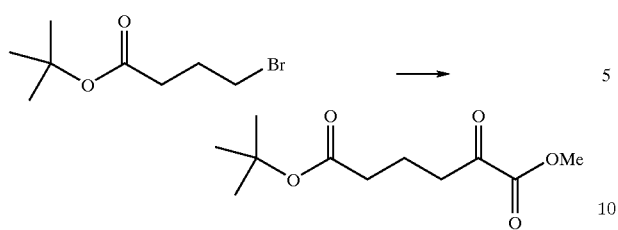

t-Butyl 4-bromobutanoate (1.22 g, 5.49 mmol), activated zinc (0.75 g in 15 ml of THF) and methyl chlorooxoacetate (0.74 ml, 6 mmol) were reacted by the same procedure as described in Example 1 for the preparation of methyl 7-tert-butyoxycarbonyl-2-oxoheptanoate to give the crude title material (1.08 g) as a colorless liquid which is used directly in next step.

Methyl 5-tert-Butoxycarbonyl-2-hydroxypentanoate

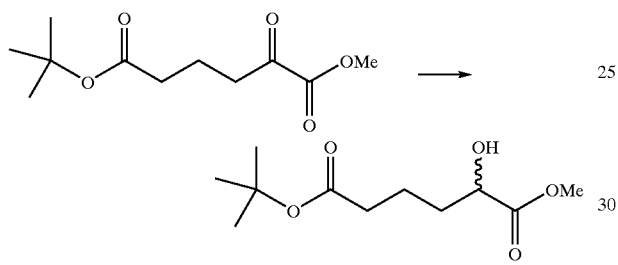

Crude methyl 5-tert-butoxycarbonyl-2-oxopentanoate (1.08 g, 4.7 mmol) and sodium triacetoxyborohydride (1.0 g, 4.7 mmol) were reacted by the same procedure as described in Example 1 for the preparation of methyl 7-tert-butoxycarbonyl-2-hydroxyheptanoate to give the title compound (854 mg, 78%, 2 steps) as a colorless liquid.

Methyl 3-[4-[3-[N-[2-Bis-(4-chlorophenyl)ethyl]-N-methylamino]propyl]phenoxy]-2-(3-tert-butoxycarbonylpropyl)-ethanoate 4-[3-[N-[2-bis-(4-chlorophenyl)ethyl]-N-methylamino] propyl]phenol (275 mg, 0.664 mmol) and methyl 5-tert-butoxycarbonyl-2-hydroxypentanoate (154 mg, 0.664 mmol) were reacted by the same procedure as described in Example 1 for the preparation of methyl 2-[4-[3-[N-[2-bis-(4-chlorophenyl)ethyl]-N-methylamino]propyl]phenoxy]-2-(5-tert-butyloxycarbonylpentyl)-ethanoate to give the title compound (140 mg, 34%) as a colorless oil.

3-[4-[3-[N-[2-Bis-(4-chlorophenyl)ethyl]-N-methylamino] propyl]phenoxy]-3-(3-tert-butyloxycarbonylpropyl)-2-methoxy-2-trimethylsilyloxy-1,1,1-trifluoropropane

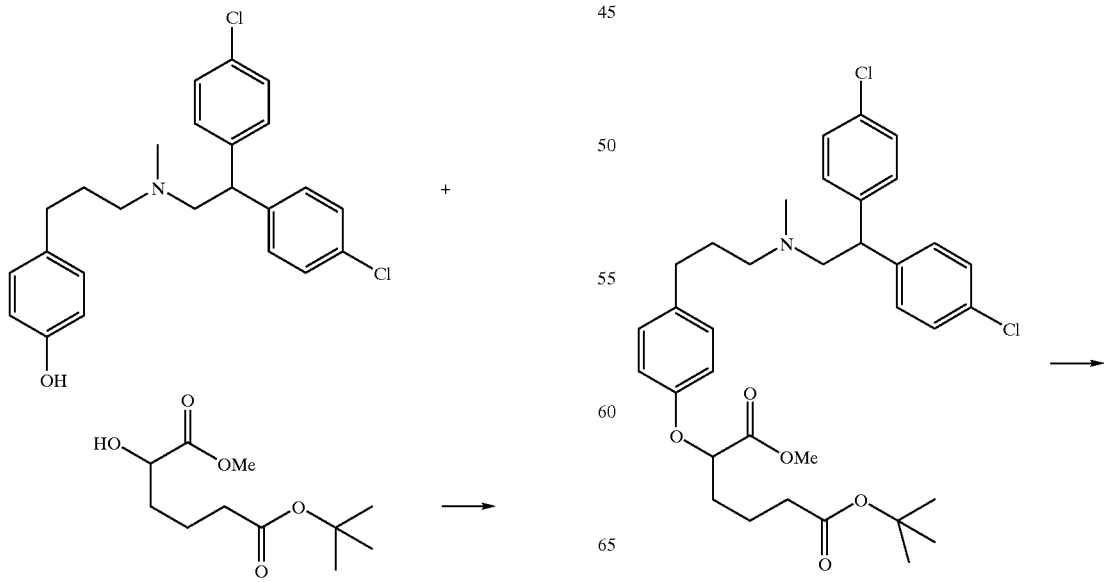

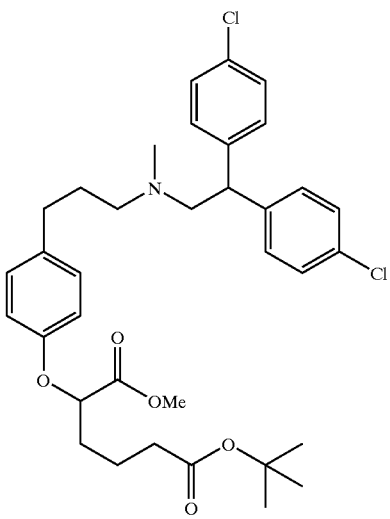

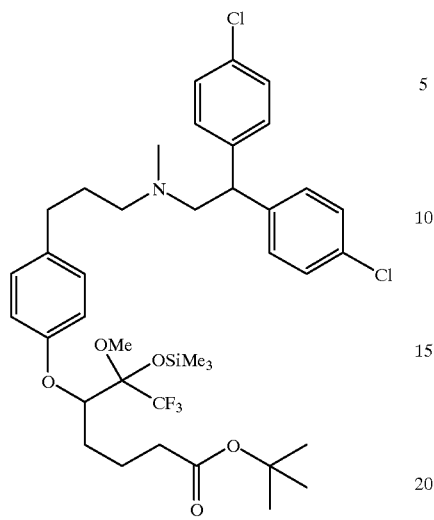

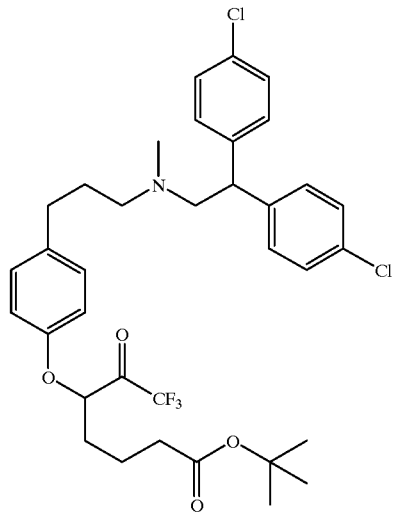

Methyl 3-[4-[3-[N-[2-Bis-(4-chlorophenyl)ethyl]-N-methylamino]propyl]phenoxy]-2-(3-tert-butoxycarbonylpropyl)-ethanoate (119 mg, 0.189 mmol) and trifluoromethyl trimethylsilane (280 µl, 1.89 mmol) were reacted by the general procedure as described in the preparation of 3-[4-[3-[N-[2-bis-(4-chlorophenyl)ethyl]-N-methylamino]propyl]phenoxy]-3-(5-tert-butyloxycarbonylpentyl)-2-methoxy-2-trimethylsilyloxy-1,1,1-trifluoropropane to give the title compound (130 mg, 89%) as a pale yellow oil.

3-[4-[3-[N-[2-Bis-(4-chlorophenyl)ethyl]-N-methylamino]propyl]phenoxy]-3-(3-tert-butyloxycarbonylpropyl)-1,1,1-trifluoro-2-propanone 3-[4-[3-[N-[2-Bis-(4-chlorophenyl)ethyl]-N-methylamino]propyl]phenoxy]-3-(3-tert-butoxycarbonylpropyl)-2-methoxy-2-trimethylsilyloxy-1,1,1-trifluoropropane (125 mg, 0.162 mmol) and a mixture of tetrabutylammonium fluoride and acetic acid (1.0 M in THF, 194 µl, 0.194 mmol) were reacted by the general procedure as described in Example 1 for the preparation of 3-[4-[3-[N-[2-Bis-(4-chlorophenyl)ethyl]-N-methylamino]propyl]phenoxy]-3-(5-tert-butyloxycarbonylpentyl)-1,1,1-trifluoro-2-propanone to give the title compound (87 mg, 81%) as a colorless oil.

3-[4-[3-[N-[2-Bis-(4-chlorophenyl)ethyl]-N-methylamino]propyl]phenoxy]-3-(3-carboxypropyl)-1,1,1-trifluoro-2-propanone, Trifluoroacetic Acid Salt

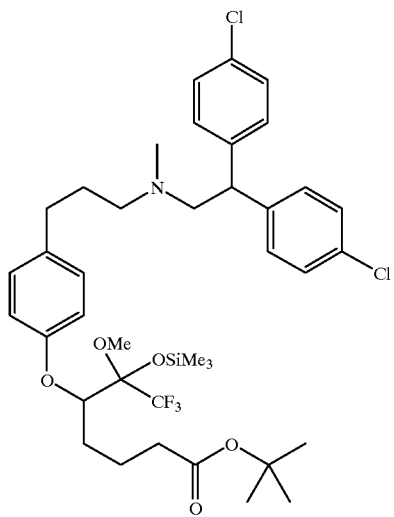

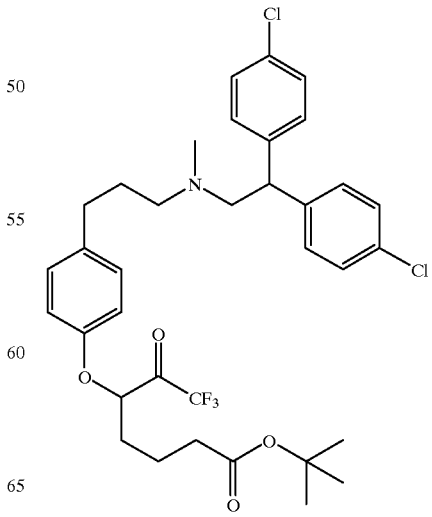

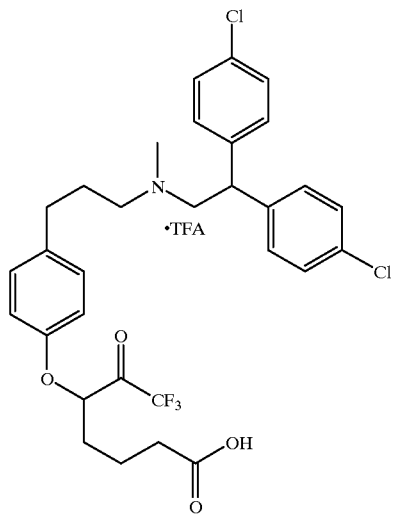

3-[4-[3-[N-[2-Bis-(4-chlorophenyl)ethyl]-N-methylamino]propyl]phenoxy]-3–4-tert-butyloxycarbonylpropyl)-1,1,1-trifluoro-2-propanone and trifluoroacetic acid were reacted by the general procedure as described in Example 1 for the preparation of 3-[4-[3-[N-[2-Bis-(4-chlorophenyl)ethyl]-N-methylamino]propyl]phenoxy]-3-(6-carboxyhexyl)-1,1,1-trifluoro-2-propanone, trifluoroacetic salt to give the title compound as a colorless syrup.

Example 3

3-[4-[3-[N-[2-Bis-(4-chlorophenyl)ethyl]-N-methylamino]propyl]phenoxy]-3-(2-carboxyethyl)-1,1,1-trifluoro-2-propanone, Trifluoroacetic Acid Salt

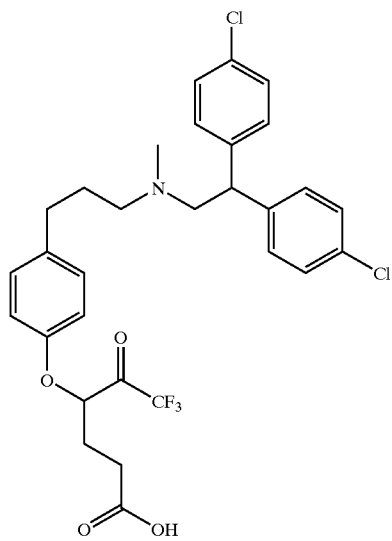

Tert-butyl 3-bromopropanoic Acid

3-Bromopropanoic acid (8.2 g, 53.6 mmol) and isobutene (60 ml) were reacted by the same procedure as described in Example 1 for the preparation of tert-butyl 6-bromohexanoate and afforded the title material (4 g, 36%) as a colorless liquid.

Methyl 4-tert-Butoxycarbonyl-2-oxobutanoate

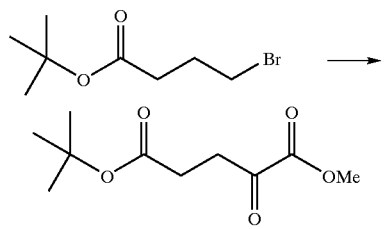

3-Bromopropanoic acid, tert-butyl ester (2.2 g, 10.6 mmol), activated zinc (1.25 g in 25 ml of THF) and methyl chlorooxoacetate (1.4 ml, 11.4 mmol) were reacted by the same procedure as described in Example 1 for the preparation of methyl 7-tert-butyoxycarbonyl-2-oxoheptanoate to give the crude title material (1.65 g) as a colorless liquid which is used directly in next step.

Methyl 4-tert-Butoxycarbonyl-2-hydroxybutanoate

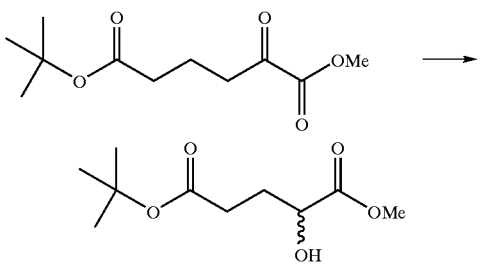

Crude methyl 4-tert-butoxycarbonyl-2-oxobutanoate (1.65 g, 7.6 mmol) and sodium triacetoxyborohydride (1.6 g, 7.6 mmol) were reacted by the same procedure as described in Example 1 for the preparation of methyl 7-tert-butoxycarbonyl-2-hydroxyheptanoate to give the title compound (460 mg, 28% 2 steps) as a colorless liquid.

Methyl 2-[4-[3-[N-[2-bis-(4-Chlorophenyl)ethyl]-N-methylamino]propyl]phenoxy]-2-(2-tert-butyloxycarbonylethyl)-ethanoate

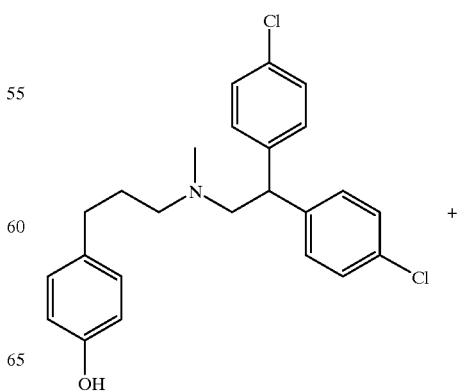

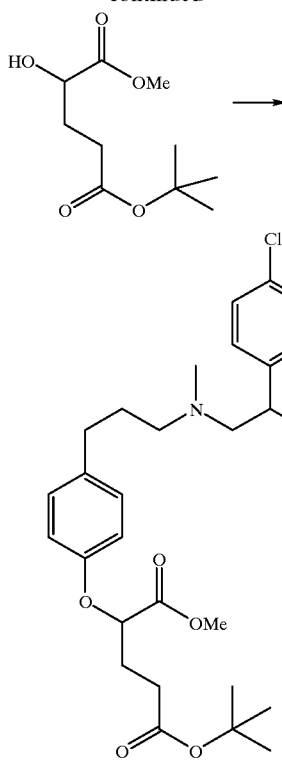

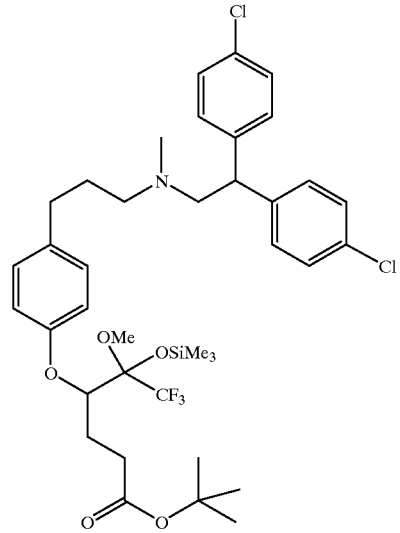

4-[3-[N-[2-bis-(4-chlorophenyl)ethyl]-N-methylamino]propyl]phenol (832 mg, 2.01 mmol) and methyl 4-tert-butoxycarbonyl-2-hydroxybutanoate (455 mg, 2.01 mmol) in benzene (10 ml) were reacted by the same procedure as described in Example 1 for the preparation of methyl 2-[4-[3-[N-[2-bis-(4-chlorophenyl)ethyl]-N-methylamino]propyl]phenoxy]-2-(5-tert-butyloxycarbonylpentyl)-ethanoate and afforded the title compound (515 mg, 42%) as a colorless oil.

3-[4-[3-[N-[2-Bis-(4-chlorophenyl)ethyl]-N-methylamino]propyl]phenoxy]-3-(2-tert-butyloxycarbonylethyl)-2-methoxy-2-trimethylsilyloxy-1,1,1-trifluoropropane Methyl 2-[4-[3-[N-[2-bis-(4-chlorophenyl)ethyl]-N-methylamino]propyl]phenoxy]-2-(2-tert-butyloxycarbonylethyl)-ethanoate (505 mg, 0.822 mmol) and trifluoromethyl trimethylsilane (0.6 ml, 4.11 mmol) were reacted by the general procedure as described in Example 1 for the preparation of 3-[4-[3-[N-[2-bis-(4-chlorophenyl)ethyl]-N-methylamino]propyl]phenoxy]-3-(5-tert-butyloxycarbonylpentyl)-2-methoxy-2-trimethylsilyloxy-1,1,1-trifluoropropane to give the title compound (600 mg, 96%) as a pale yellow oil.

3-[4-[3-[N-[2-Bis-(4-chlorophenyl)ethyl]-N-methylamino]propyl]phenoxy]-3-(2-tert-butyloxycarbonylethyl)-1,1,1-trifluoro-2-propanone

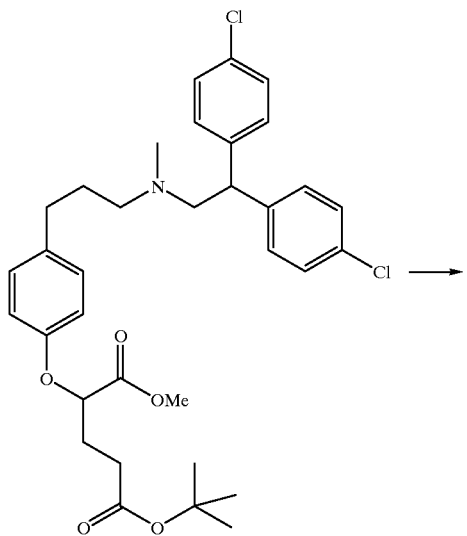

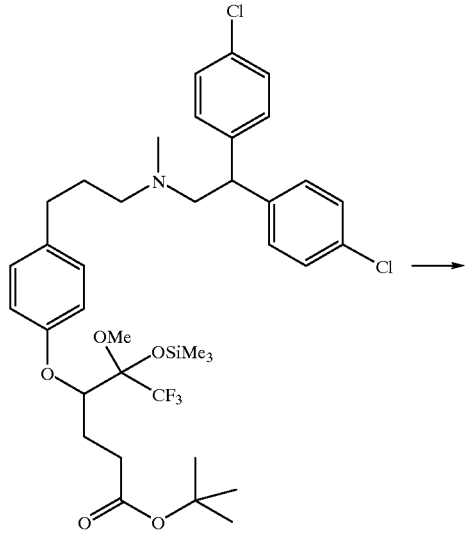

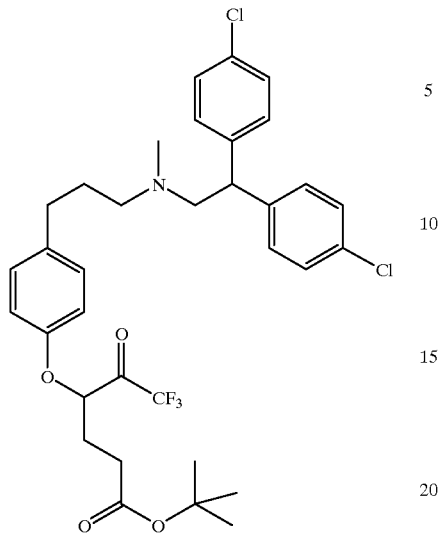

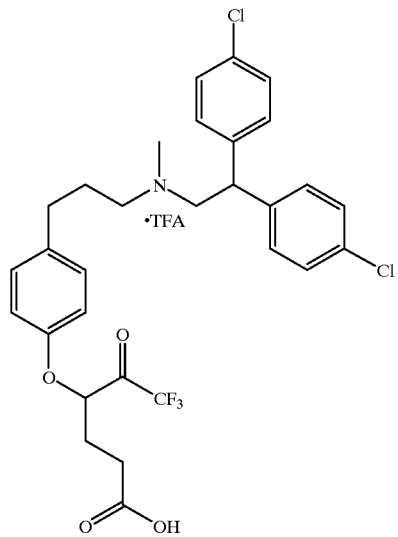

3-[4-[3-[N-[2-Bis-(4-chlorophenyl)ethyl]-N-methylamino]propyl]phenoxy]-3-(2-tert-butyloxycarbonylethyl)-2-methoxy-2-trimethylsilyloxy-1,1,1-trifluoropropane (150 mg, 0.198 mmol) and a mixture of tetrabutylammonnium fluoride and acetic acid (1.0 M in THF, 240 µl, 0.24 mmol) were reacted by the general procedure as described in Example 1 for the preparation of 3-[4-[3-[N-[2-bis-(4-chlorophenyl)ethyl]-N-methylamino]propyl]phenoxy]-3-(5-tert-butyloxycarbonylpentyl)-1,1,1-trifluoro-2-propanone to give the title compound (120 mg, 93%) as a pale yellow oil.

Treatment of the above free amine with anhydrous hydrogen chloride (1.0 M in ether) gave the hydrochloride salt as a pale yellow syrup.

3-[4-[3-[N-[2-Bis-(4-Chlorophenyl)ethyl]-N-methylamino]propyl]phenoxy]-3-(2-carboxyethyl)-1,1,1-trifluoro-2-propanone, Trifluoroacetic Acid Salt

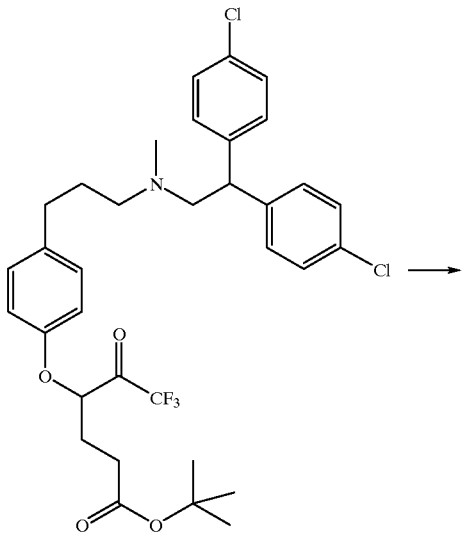

3-[4-[3-[N-[2-Bis-(4-chlorophenyl)ethyl]-N-methylamino]propyl]phenoxy]-3-(2-tert-butyloxycarbonylethyl)-1,1,1-trifluoro-2-propanone was reacted by the general procedure as described in Example 1 for the preparation of 3-[4-[3-[N-[2-bis-(4-chlorophenyl)ethyl]-N-methylamino]propyl]phenoxy]-3-(5-carboxypentyl)-1,1,1-trifluoro-2-propanone, trifluoroacetic salt to give the title compound as a pale yellow sticky solid.

Example 4

3-[4-[3-[N-[2-Bis-(4-Chlorophenyl)ethyl]-N-methylamino]propyl]phenoxy]-3-(3-carboxyphenylethyl)-1,1,1-trifluoro-2-propanone, Trifluoroacetic Acid Salt

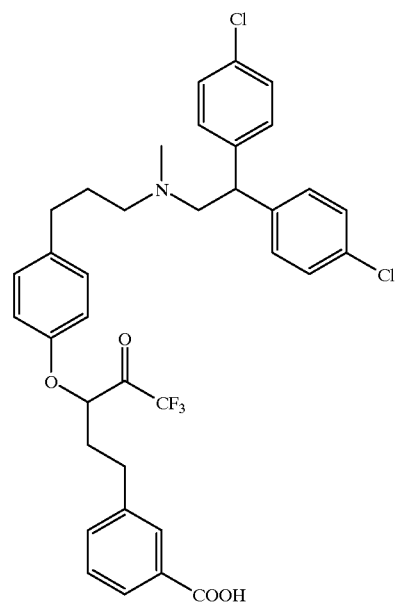

t-Butyl 3-Iodobenzoate

3-Iodobenzoic (5 g, 20 mmol) acid and iso-butene (30 ml) were reacted by the same procedure as described in Example 1 for the preparation of tert-butyl 6-bromohexanoate and afforded the title material (4.2 g, 68%) as a pale yellow oil.

Methyl 4-(3-tert-Butoxycarbonylphenyl)butanoate

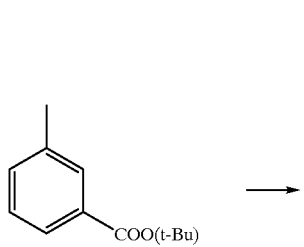 → 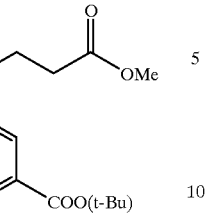

A mixture of tert-butyl 3-iodobenzoate (2 g, 6.58 mmol) and tetrakis(triphenylphosphine)palladium(0) (250 mg, 0.329 mmol) in THF (10 ml) was treated with a freshly prepared 3-methoxycarbonylpropylzinc iodide (0.25 M in THF, 27 ml, 6.58 mmol). The mixture was stirred at room temperature for 3 hours, quenched with saturated aqueous ammonium chloride (5 ml) and extracted with diethyl ether. The organic phase was washed with saturated aqueous ammonium chloride, brine, dried over sodium sulfate and concentrated in vacuo. The residue was chromatographed on silica gel (hexane:ethyl acetate=9:1) to give the title material (0.73 g, 40%) as a colorless oil.

Methyl 4-(3-tert-Butoxycarbonylphenyl)-2-hydroxybutanoate

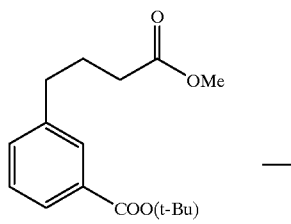 → 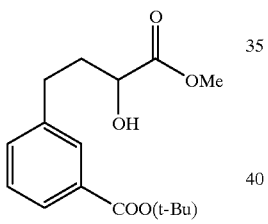

To a solution of methyl 4-(3-tert-butoxycarbonylphenyl) butanoate (200 mg, 0.71 mmol) in THF (2 ml) at −78° C. was added dropwise potasium bis(trimethyl)amide (0.5 M in toluene, 1.6 ml, 0.8 mmol). The mixture was stirred at this temperature for 0.5 hours and treated with dropwise addition of a solution of trans-2-phenylsulfonyl-3-phenyloxaziridine (223 mg, 0.8 mmol) in THF (2 ml). The mixture was stirred at −78° C. for 3 hours, quenched with aqueous ammonium chloride, warmed room temperature and diluted with ethyl acetate. The organic phase was washed with aqueous ammonium chloride, brine, dried over sodium sulfate and concentrated in vacuo. The residue was chromatographed on silica gel (hexane:ethyl acetate=9:1) to give the title compound (90 mg, 43%) as a pale yellow oil.

Methyl 3-[4-[3-[N-[2-Bis-(4-Chlorophenyl)ethyl]-N-methylamino]propyl]phenoxy]-2-(3-tert-butoxycarbonylphenylethyl)-ethanoate

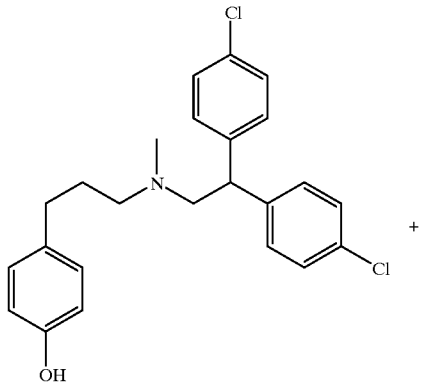

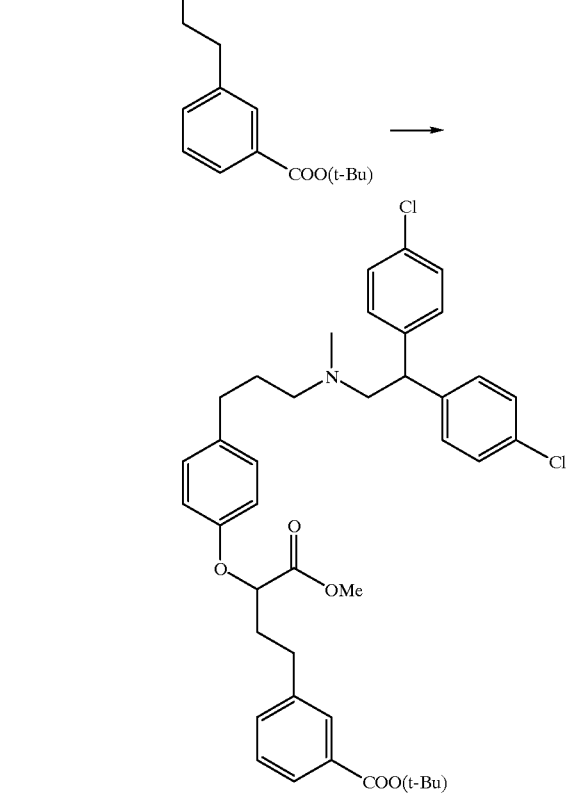

4-[3-[N-[2-bis-(4-chlorophenyl)ethyl]-N-methylamino] propyl]phenol (320 mg, 0.77 mmol) and methyl 4-(3-tert-butoxycarbonylphenyl)-2-hydroxybutanoate (175 mg, 0.59 mmol) in benzene (3 ml) were reacted by the same procedure as described in Example 1 for the preparation of methyl 2-[4-[3-[N-[2-Bis-(4-chlorophenyl)ethyl]-N-methylamino] propyl]phenoxy]-2-(5-tert-butoxycarbonylpentyl)-ethanoate and afforded the title compound (205 mg, 49%) as a pale yellow oil.

3-[4-[3-[N-[2-Bis-(4-Chlorophenyl)ethyl]-N-methylamino] propyl]phenoxy]-3-(3-tert-butyloxycarbonylphenylethyl)-2-methoxy-2-trimethylsilyloxy-1,1,1-trifluoropropane

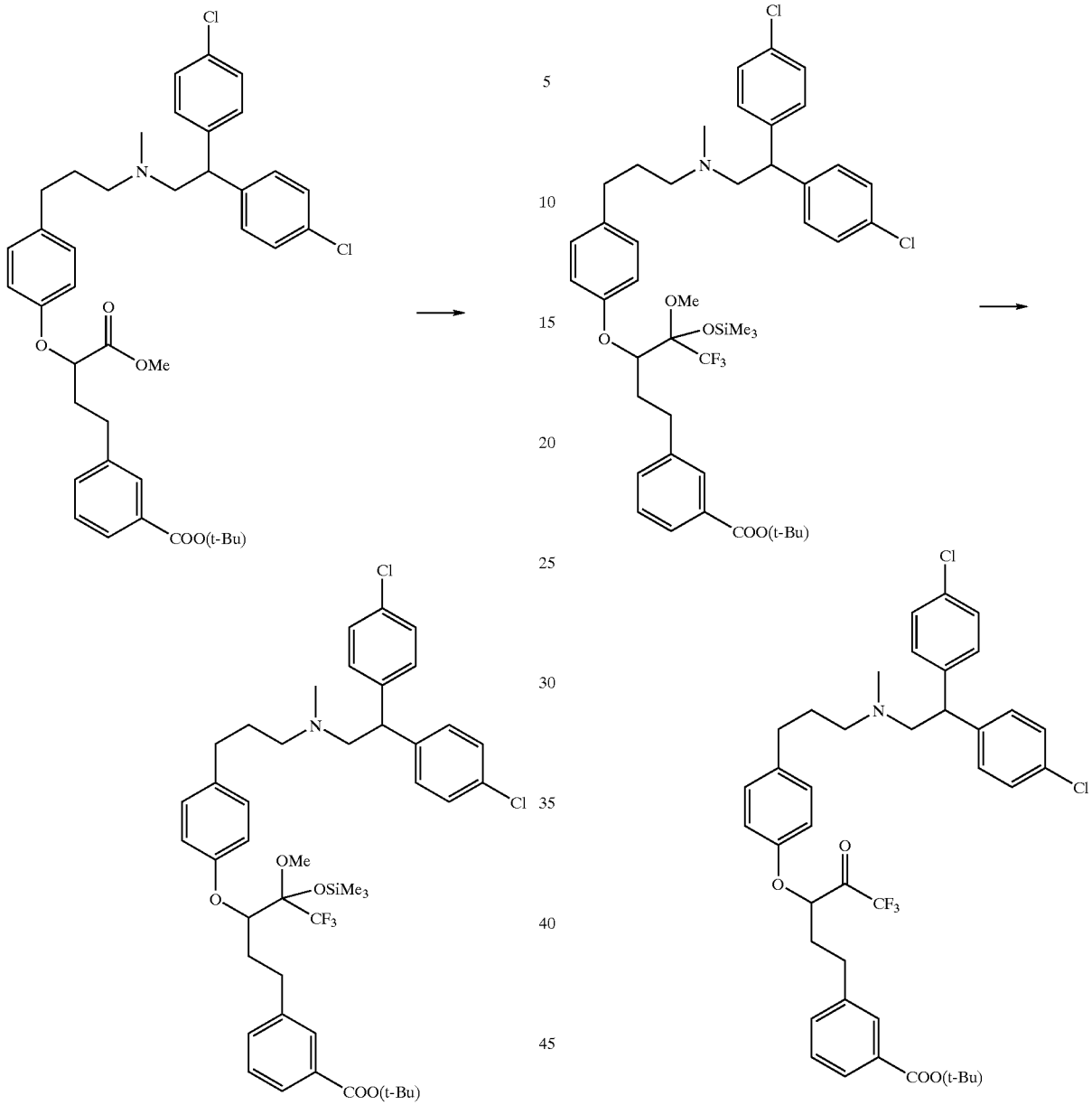

Methyl 3-[4-[3-[N-[2-Bis-(4-chlorophenyl)ethyl]-N-methylamino]propyl]phenoxy] 2-(3-tert-butoxycarbonylphenylethyl)-ethanoate (150 mg, 0.22 mmol) and trifluoromethyl trimethylsilane (0.235 ml, 2.2 mmol) were reacted by the general procedure as described in Example 1 for the preparation of 3-[4-[3-[N-[2-bis-(4-chlorophenyl)ethyl]-N-methylamino]propyl]phenoxy]-3-(5-tert-butyloxycarbonylpentyl)-2-methoxy-2-trimethylsilyloxy-1,1,1-trifluoropropane to give the title compound (103 mg, 56%) as a pale yellow oil.

3-[4-[3-[N-[2-Bis-(4-Chlorophenyl)ethyl]-N-methylamino]propyl]phenoxy]-3-(3-tert-butyloxycarbonylphenylethyl)-1,1,1-trifluoro-2-propanone 3-[4-[3-[N-[2-Bis-(4-chlorophenyl)ethyl]-N-methylamino]propyl]phenoxy]-3-(3-tert-butyloxycarbonylphenylethyl)-2-methoxy-2-trifluoromethylsilyloxy-1,1,1-trifluoropropane (100 mg, 0.12 mmol) and a mixture of tetrabutylammonium fluoride and acetic acid (1.0 M in THF, 160 μl, 0.16 mmol) were reacted by the general procedure as described in Example 1 for the preparation of 3-[4-[3-[N-[2-bis-(4-chlorophenyl)ethyl]-N-methylamino]propyl]phenoxy]-3-(5-tert-butyloxycarbonylpentyl)-1,1,1-trifluoro-2-propanone to give the title compound (63 mg, 72%) as a colorless oil.

3-[4-[3-[N-[2-Bis-(4-Chlorophenyl)ethyl]-N-methylamino]propyl]phenoxy]-3-(3-carboxyphenylethyl)-1,1,1-trifluoro-2-propanone, Trifluoroacetic Acid Salt

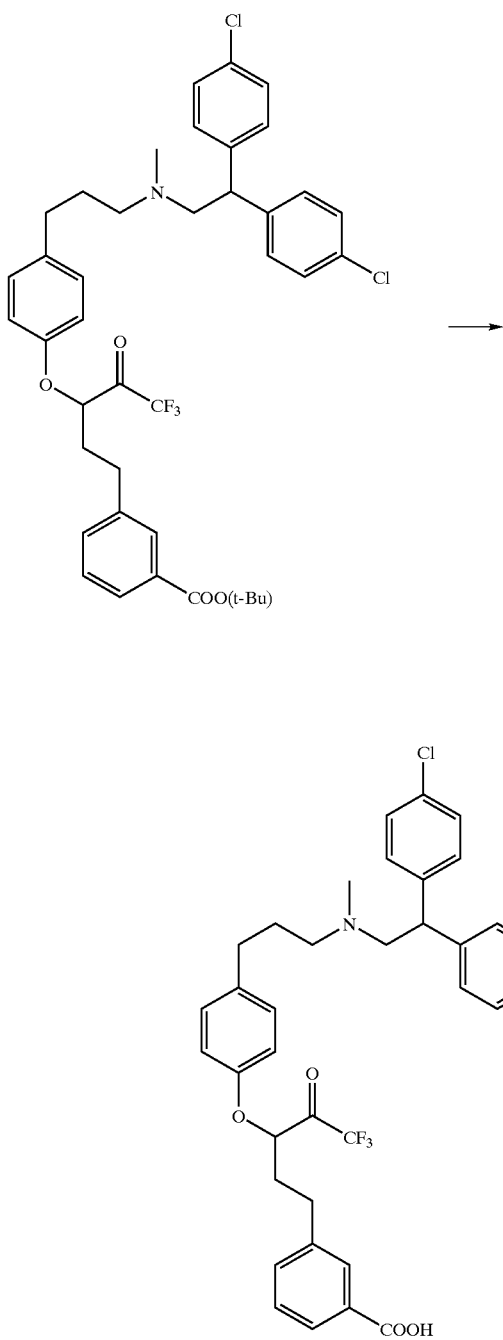

3-[4-[3-[N-[2-Bis-(4-chlorophenyl)ethyl]-N-methylamino]propyl]phenoxy]-3-(3-tert-butyloxycarbonylphenylethyl)-1,1,1-trifluoro-2-propanone (60 mg, 0.08 mmol) and trifluoroacetic acid were reacted by the general procedure as described in Example 1 for the preparation of 3-[4-[3-[N-[2-bis-(4-chlorophenyl)ethyl]-N-methylamino]propyl]phenoxy]-3-(5-carboxypentyl)-1,1,1-trifluoro-2-propanone, trifluoroacetic acid salt to give the title compound (65 mg, 100%) as a white foamy solid.

What is claimed:
1. A compound of the formula

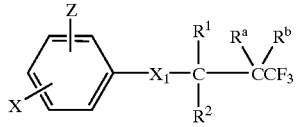

I wherein:

X$_1$ is O or S(O)$_n$;

n is 0, 1 or 2;

R$^a$ and R$^b$ when taken together form an oxo (=O) group, or R$^a$ and R$^b$ are each independently hydrogen or OH;

X is H, CF$_3$, halogen, NR$^3$R$^4$, NH(CO)NHR$^3$R$^4$, C(O)NR$^3$R$^4$, OH, OR$^8$, SH, S(O)$_n$R$^8$, C(O)OR$^6$, NH(CO)OR$^8$, C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being optionally substituted by COOR$^6$, CN, C(O)NR$^3$R$^4$, PO$_3$R$^6$, SO$_3$R$^6$, heterocyclic, OH, OR$^8$, SH, S(O)$_n$R$^8$, NR$^3$R$^4$, NH(CO)NR$^3$R$^4$, NH(CO)OR$^8$, OC(O)OR$^8$, aryl or heteroaryl, said aryl or heteroaryl being optionally substituted by one or two groups independently selected from COOR$^6$, SO$_3$R$^6$, OCOR$^6$, PO$_3$R$^6$ or heterocyclic;

R$^1$ and R$^2$ are each independently H, substituted C$_1$–C$_7$ alkyl, C$_2$–C$_7$ alkenyl, C$_2$–C$_7$ alkynyl or C$_3$–C$_7$ cycloalkyl, said alkyl group being substituted by, and said alkenyl, alkynyl or cycloalkyl group being optionally substituted by, COOR$^6$, CN, C(O)NR$^3$R$^4$, PO$_3$R$^6$, SO$_3$R$^6$, heterocyclic, OH, OR$^8$, SH, S(O)$_n$R$^8$, NR$^3$R$^4$, NH(CO)NR$^3$R$^4$, NH(CO)OR$^7$, OC(O)OR$^7$, aryl or heteroaryl, said aryl or heteroaryl group being optionally substituted by one or two groups independently selected from COOR$^6$, SO$_3$R$^6$, PO$_3$R$^6$ or heterocyclic;

R$^3$ and R$^4$ are each independently H, C$_1$–C$_7$ alkyl, C$_2$–C$_7$ alkenyl, C$_2$–C$_7$ alkynyl, C$_3$–C$_7$ cycloalkyl, heterocyclic or aryl, said alkyl, alkenyl, alkynyl, cycloalkyl, heterocyclic or aryl group being optionally substituted with COOR$^6$, CN, OR$^6$, NR$^6$R$^7$, SO$_3$R$^6$, PO$_3$R$^6$, halogen, aryl or heteroaryl, said aryl or heteroaryl substituent being optionally substituted with one or two groups independently selected from COOR$^6$, SO$_3$R$^6$, PO$_3$R$^6$ or heterocyclic;

R$^5$ is H, C$_1$–C$_7$ alkyl or C$_3$–C$_7$ cycloalkyl, said alkyl or cycloalkyl group being optionally substituted by COOR$^6$, CN, C(O)NR$^3$R$^4$, PO$_3$R$^6$, SO$_3$R$^6$, heterocyclic, OR$^3$, S(O)$_n$R$^8$, NR$^3$R$^4$, NH(CO)NR$^3$R$^4$, NH(CO)OR$^8$, C(O)$_2$OR$^8$, aryl or heteroaryl, said aryl or heteroaryl group being optionally substituted by one or two groups independently selected from COOR$^6$, SO$_3$R$^6$, PO$_3$R$^6$ or heterocyclic;

R$^6$ and R$^7$ are independently H, C$_1$–C$_7$ alkyl or C$_3$–C$_7$ cycloalkyl;

R$^8$ is the same as R$^3$ but cannot be H;

Z is OR$^9$, S(O)$_n$R$^9$, NR$^9$R$^{10}$ or CHR$^9$R$^{10}$;

R$^9$ and R$^{10}$ are each independently hydrogen, C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being optionally substituted with NR$^{11}$R$^{12}$, SR$^{11}$, S(O)R$^{16}$, SO$_2$R$^{16}$ or OR$^{11}$, with the proviso that both R$^9$ and R$^{10}$ may not both be hydrogen;

$R^{11}$ and $R^{12}$ are each independently H, $C_1$–$C_7$ alkyl, $C_2$–$C_7$ alkenyl, $C_2$–$C_7$ alkynyl, $C_3$–$C_7$ cycloalkyl or aryl, said alkyl, alkenyl, alkynyl, cycloalkyl or aryl group being optionally substituted by 1–3 $COOR^6$, $OR^6$, $SiR^{13}R^{14}R^{15}$, $OR^{13}$, aryl, biaryl or heteroaryl, said aryl, biaryl or heteroaryl group being optionally substituted with 1–3 halogen, $CF_3$, $OR^6$, $COOR^6$, $NO_2$ or CN, or $R^{11}$ and $R^{12}$ taken together with the nitrogen to which they are attached form a 5–7 membered heterocyclic ring with one or more O, N or S heteroatoms, said heterocyclic ring being optionally substituted with $COOR^6$ or $C_1$–$C_5$ alkyl optionally substituted with $OR^6$, $COOR^6$ or $C(O)NR^3R^4$; and $R^{13}$, $R^{14}$ and $R^{15}$ are each independently aryl, benzyl, benzhydryl, biaryl, heteroaryl, aryl($C_1$–$C_6$)alkyl or heteroaryl($C_1$–$C_6$)alkyl, said aryl group being optionally substituted with halogen, $CF_3$, $OR^6$, $COOR^6$, $NO_2$, CN or $C_1$–$C_7$ alkyl;

$R^{16}$ is the same as $R^{11}$ and $R^{12}$ but is not hydrogen; or a pharmaceutically acceptable salt thereof, with the proviso that $R^1$ and $R^2$ may not both be hydrogen.

2. A compound of claim 1 wherein $R^1$ is H.
3. A compound of claim 2 wherein $X_1$ is O.
4. A compound of claim 2 in which $X_1$ is $S(O)_n$ in which n is 0, 1 or 2.
5. A compound of the formula

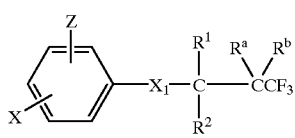

I wherein:

$X_1$ is O or $S(O)_n$;

n is 0, 1 or 2;

$R^a$ and $R^b$ when taken together form an oxo (=O) group, or $R^a$ and $R^b$ are each independently hydrogen or OH;

X is H;

$R^1$ is H;

$R^2$ is $C_1$–$C_7$ alkyl substituted by COOH or $C_1$–$C_7$ alkyl substituted by carboxy-substituted phenyl;

Z is $OR^9$, $S(O)_nR^9$, $NR^9R^{10}$ or $CHR^9R^{10}$;

$R^9$ and $R^{10}$ are each independently hydrogen, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted with $NR^{11}R^{12}$, $SR^{11}$, $S(O)R^{16}$, $SO_2R^{16}$ or $OR^{11}$, with the proviso that both $R^9$ and $R^{10}$ may not both be hydrogen;

$R^{11}$ and $R^{12}$ are each independently H, $C_1$–$C_7$ alkyl, $C_2$–$C_7$ alkenyl, $C_2$–$C_7$ alkynyl, $C_3$–$C_7$ cycloalkyl or aryl, said alkyl, alkenyl, alkynyl, cycloalkyl or aryl group being optionally substituted by 1–3 $COOR^6$, $OR^6$, $SiR^{13}R^{14}R^{15}$, $OR^{13}$, aryl, biaryl or heteroaryl, said aryl, biaryl or heteroaryl group being optionally substituted with 1–3 halogen, $CF_3$, $OR^6$, $COOR^6$, $NO_2$ or CN, or $R^{11}$ and $R^{12}$ taken together with the nitrogen to which they are attached form a 5–7 membered heterocyclic ring with one or more O, N or S heteroatoms, said heterocyclic ring being optionally substituted with $COOR^6$ or $C_1$–$C_5$ alkyl optionally substituted with $OR^6$, $COOR^6$ or $C(O)NR^3R^4$;

$R^6$ and $R^7$ are independently H, $C_1$–$C_7$ alkyl or $C_3$–$C_7$ cycloalkyl;

$R^{13}$, $R^{14}$ and $R^{15}$ are each independently aryl, benzyl, benzhydryl, biaryl, heteroaryl, aryl($C_1$–$C_6$)alkyl or heterocyclic($C_1$–$C_6$)alkyl, said aryl group being optionally substituted with halogen, $CF_3$, $OR^6$, $COOR^6$, $NO_2$, CN or $C_1$–$C_7$ alkyl;

$R^3$ and $R^4$ are each independently H, $C_1$–$C_7$ alkyl, $C_2$–$C_7$ alkenyl, $C_2$–$C_7$ alkynyl, $C_3$–$C_7$ cycloalkyl, heterocyclic or aryl, said alkyl, alkenyl, alkynyl, cycloalkyl, heterocyclic or aryl group being optionally substituted with $COOR^6$, CN, $OR^6$, $NR^6R^7$, $SO_3R^6$, $PO_3R^6$, halogen, aryl or heteroaryl, said aryl or heteroaryl substituent being optionally substituted with one or two groups independently selected from $COOR^6$, $SO_3R^6$, $PO_3R^6$ or heterocyclic; and $R^{16}$ is the same as $R^{11}$ and $R^{12}$ but is not hydrogen; or a pharmaceutically acceptable salt thereof.

6. A compound of any of claims 1–5 wherein:

Z is Y—$Z^1$;

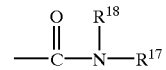

Y is —O—, —S(O)$_{\overline{n}}$—, —N— or —CH$_2$;

$R^c$ is H, —$COCF_3$, —$COC_6H_5$, —$COO(C_1$–$C_6)$alkyl,

in which $R^{18}$ and $R^{17}$ are each independently H or $(C_1$–$C_6)$alkyl, $(C_1$–$C_{18})$alkyl or $(C_1$–$C_{18})$alkyl substituted by one or more of phenyl or phenyl substituted by 1–5 fluoro, 1–3 halo (other than fluoro), 1–3 $(C_1$–$C_6)$ alkoxy, 1–3 $(C_1$–$C_6)$alkyl, 1–3 nitro, 1–3 cyano, 1–3 hydroxy, 1–3 trifluoromethyl, 1–3 $(C_1$–$C_6)$alkylthio, 1–3 amino, 1–3 $(C_1$–$C_6)$alkylamino, 1–3 di$(C_1$–$C_6)$ alkylamino, 1–3 carboxyl, 1–3 —$COO(C_1$–$C_6)$alkyl, 1–3 —$SO_3H$, 1–3 —$SO_2NHR^{19}$ in which $R^{19}$ is H or $(C_1$–$C_6)$alkyl, or

in which $R^{18}$ and $R^{17}$ are as defined above;

$Z^1$ is (a)

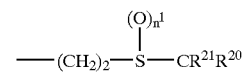

in which $n^1$ is 0, 1 or 2 and $R^{21}$ and $R^{20}$ are phenyl or phenyl substituted by 1–5 fluoro, 1–3 halo (other than fluoro), 1–3 $(C_1$–$C_6)$alkoxy, 1–3 $(C_1$–$C_6)$alkyl, 1–3 nitro, 1–3 cyano, 1–3 hydroxy, 1–3 trifluoromethyl, 1–3 $(C_1$–$C_6)$alkylthio, 1–3 amino, 1–3 $(C_1$–$C_6)$alkylamino, 1–3 di$(C_1$–$C_6)$alkylamino, 1–3 carboxy, 1–3 —$COO(C_1$–$C_6)$alkyl, 1–3 —$SO_3H$, 1–3 —$SO_2NHR^{19}$ in which $R^{19}$ is as defined above, or

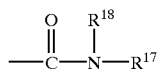

in which $R^{18}$ and $R^{17}$ are as defined above;

(b)

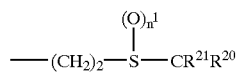

in which $n^1$ is 0, 1 or 2 and $R^{21}$ and $R^{20}$ are as defined above;

(c)

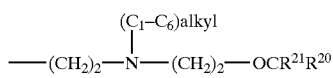

in which $R^{21}$ and $R^{20}$ are as defined above;

(d)

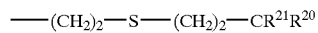

in which $R^{21}$ and $R^{20}$ are as defined above;

(e)

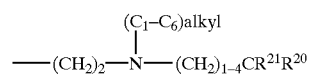

in which $R^{21}$ and $R^{20}$ are as defined above; or (f)

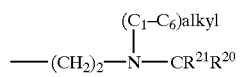

in which $R^{21}$ and $R^{20}$ are as defined above.

7. A compound of the formula

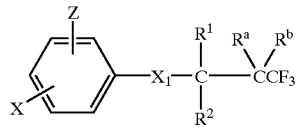

I wherein:

$X_i$ is O or $S(O)_n$;

n is 0, 1 or 2;

$R^a$ and $R^b$ when taken together form an oxo (=O) group, or $R^a$ and $R^b$ are each independently hydrogen or OH;

X is H, $CF_3$, halogen, $NR^3R^4$, $NH(CO)NHR^3R^4$, $C(O)NR^3R^4$, OH, $OR^8$, SH, $S(O)_nR^8$, $C(O)OR^6$, $NH(CO)OR^8$, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^6$, CN, $C(O)NR^3R^4$, $PO_3R^6$, $SO_3R^6$, heterocyclic, OH, $OR^8$, SH, $S(O)_nR^8$, $NR^3R^4$, $NH(CO)NR^3R^4$, $NH(CO)OR^8$, $OC(O)OR^8$, aryl or heteroaryl, said aryl or heteroaryl being optionally substituted by one or two groups independently selected from $COOR^6$, $SO_3R^6$, $OCOR^6$, $PO_3R^6$ or heterocyclic;

$R^1$ and $R^2$ are each independently H, substituted $C_1$–$C_7$ alkyl, $C_2$–$C_7$ alkenyl, $C_2$–$C_7$ alkynyl or $C_3$–$C_7$ cycloalkyl, said alkyl group being substituted by, and said alkenyl, alkynyl or cycloalkyl group being optionally substituted by, $COOR^6$, CN, $C(O)NR^3R^4$, $PO_3R^6$, $SO_3R^6$, heterocyclic, OH, $OR^8$, SH $S(O)_nR^8$, $NR^3R^4$, $NH(CO)NR^3R^4$, $NH(CO)OR^7$, $OC(O)OR^7$, aryl or heteroaryl, said aryl or heteroaryl group being optionally substituted by one or two groups independently selected from $COOR^6$, $SO_3R^6$, $PO_3R^6$ or heterocyclic;

$R^3$ and $R^4$ are each independently H, $C_1$–$C_7$ alkyl, $C_2$–$C_7$ alkenyl, $C_2$–$C_7$ alkynyl, $C_3$–$C_7$ cycloalkyl, heterocyclic or aryl, said alkyl, alkenyl, alkynyl, cycloalkyl, heterocyclic or aryl group being optionally substituted with $COOR^6$, CN, $OR^6$, $NR^6R^7$, $SO_3R^6$, $PO_3R^6$, halogen, aryl or heteroaryl, said aryl or heteroaryl substituent being optionally substituted with one or two groups independently selected from $COOR^6$, $SO_3R^6$, $PO_3R^6$ or heterocyclic;

$R^6$ and $R^7$ are independently H, $C_1$–$C_7$ alkyl or $C_3$–$C_7$ cycloalkyl;

$R^8$ is the same as $R^3$ but cannot be H; and

Z is

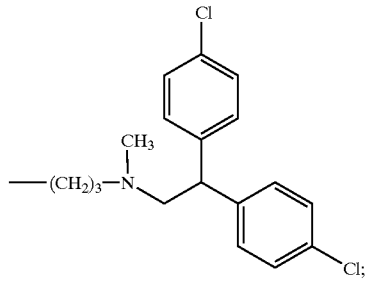

or a pharmaceutically acceptable salt thereof, with the proviso that $R^1$ and $R^2$ may not both be hydrogen.

8. A pharmaceutical composition for the inhibition of cytosolic phospholipase $A_2$ comprising a therapeutically effective amount of a compound of claim 1 and a pharmaceutically acceptable carrier.

9. A method of inhibiting cytosolic phospholipase $A_2$ in a mammal in need thereof, comprising administering to said mammal a therapeutically effective amount of a compound of claim 1.

* * * * *